US010124009B2

(12) United States Patent
Landau et al.

(10) Patent No.: US 10,124,009 B2
(45) Date of Patent: Nov. 13, 2018

(54) BROMODOMAIN INHIBITORS

(71) Applicant: Tensha Therapeutics, Inc., South San Francisco, CA (US)

(72) Inventors: Steven B. Landau, Wellesley, MA (US); Michael Kagey, Arlington, MA (US)

(73) Assignee: Tensha Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 15/522,222

(22) PCT Filed: Oct. 27, 2015

(86) PCT No.: PCT/US2015/057538
§ 371 (c)(1),
(2) Date: Apr. 26, 2017

(87) PCT Pub. No.: WO2016/069578
PCT Pub. Date: May 6, 2016

(65) Prior Publication Data
US 2017/0333444 A1  Nov. 23, 2017

Related U.S. Application Data

(60) Provisional application No. 62/068,983, filed on Oct. 27, 2014.

(51) Int. Cl.
*A61K 31/551* (2006.01)
*C07D 495/14* (2006.01)
*C07D 243/10* (2006.01)
*C07D 255/04* (2006.01)

(52) U.S. Cl.
CPC .......... *A61K 31/551* (2013.01); *C07D 243/10* (2013.01); *C07D 255/04* (2013.01); *C07D 495/14* (2013.01)

(58) Field of Classification Search
CPC ............................ A61K 31/551; C07D 495/14
USPC .......................................... 514/220; 540/560
See application file for complete search history.

(56) References Cited

U.S. PATENT DOCUMENTS

| | | | |
|---|---|---|---|
| 2,951,540 A | 9/1960 | Hawkins | |
| 3,681,343 A | 8/1972 | Hester, Jr. | |
| 3,709,898 A | 1/1973 | Hester, Jr. | |
| 3,812,259 A | 5/1974 | Collins | |
| 4,621,083 A | 11/1986 | Casals-Stenzel et al. | |
| 5,104,543 A | 4/1992 | Brandt et al. | |
| 5,593,986 A | 1/1997 | Tahara et al. | |
| 5,712,274 A | 1/1998 | Sueoka et al. | |
| 5,721,231 A | 2/1998 | Moriwaki et al. | |
| 5,753,649 A | 5/1998 | Tahara et al. | |
| 5,760,032 A | 6/1998 | Kitajima et al. | |
| 5,846,972 A | 12/1998 | Buckman et al. | |
| 5,854,238 A | 12/1998 | Kempen | |
| 6,312,215 B1 | 11/2001 | Walker | |
| 6,444,664 B1 | 9/2002 | Princen et al. | |
| 6,861,422 B2 | 3/2005 | Hoffmann et al. | |
| 7,015,213 B1 | 3/2006 | Bigg et al. | |
| 7,528,143 B2 | 5/2009 | Noronha et al. | |
| 7,528,153 B2 | 5/2009 | Aerts | |
| 7,589,167 B2 | 9/2009 | Zhou et al. | |
| 7,750,152 B2 | 7/2010 | Hoffman et al. | |
| 7,786,299 B2 | 8/2010 | Hoffmann et al. | |
| 7,816,530 B2 | 10/2010 | Grauert | |
| 7,825,246 B2 | 11/2010 | Noronha et al. | |
| 8,003,786 B2 | 8/2011 | Hoffmann et al. | |
| 8,044,042 B2 | 10/2011 | Adachi et al. | |
| 8,133,900 B2 | 3/2012 | Hood et al. | |
| 8,138,199 B2 | 3/2012 | Noronha et al. | |
| 8,338,464 B2 | 12/2012 | Melnick et al. | |
| 8,476,260 B2 | 7/2013 | Miyoshi et al. | |
| 8,604,042 B2 | 12/2013 | Noronha et al. | |
| 8,981,083 B2 | 3/2015 | Bradner et al. | |
| 9,301,962 B2 | 4/2016 | Bradner et al. | |

(Continued)

FOREIGN PATENT DOCUMENTS

| | | |
|---|---|---|
| CA | 2020806 A1 | 1/1991 |
| CA | 2710740 A1 | 7/2009 |
| CH | 622019 A5 | 3/1981 |
| CN | 1227555 A | 9/1999 |

(Continued)

OTHER PUBLICATIONS

Final Rejection for U.S. Appl. No. 13/697,963, "Compositions and Methods for Modulating Metabolism," dated Aug. 21, 2015.

(Continued)

*Primary Examiner* — Brenda L Coleman
(74) *Attorney, Agent, or Firm* — Foley Hoag LLP

(57) ABSTRACT

The present invention relate to bromodomain inhibitor compounds, pharmaceutical compositions comprising the bromodomain inhibitor compounds and methods of treating a disorder responsive to fee modulation of a BET family polypeptide using the compounds and pharmaceutical compositions described. (Formula (I))

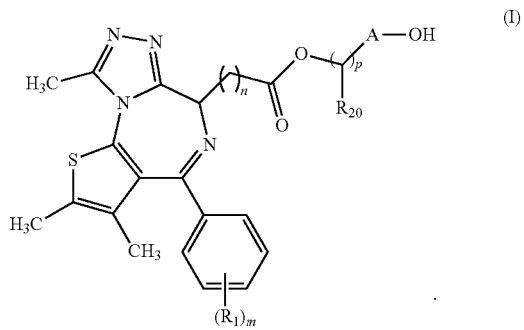

10 Claims, 12 Drawing Sheets

(56) References Cited

U.S. PATENT DOCUMENTS

| | | | |
|---|---|---|---|
| 9,320,711 B2 | 4/2016 | Natoli et al. |
| 9,320,741 B2 | 4/2016 | Bradner et al. |
| 9,763,956 B2 | 9/2017 | Bernstein et al. |
| 9,789,120 B2 | 10/2017 | Bradner et al. |
| 9,815,849 B2 | 11/2017 | Bradner et al. |
| 2002/0032200 A1 | 3/2002 | Cai et al. |
| 2002/0169158 A1 | 11/2002 | Hunt et al. |
| 2003/0130268 A1 | 7/2003 | Sagara et al. |
| 2003/0216758 A1 | 11/2003 | Signore |
| 2004/0043378 A1 | 3/2004 | Zhou et al. |
| 2004/0176380 A1 | 9/2004 | Hoffmann et al. |
| 2006/0074088 A1 | 4/2006 | Munzert et al. |
| 2006/0142257 A1 | 6/2006 | Nieschlag et al. |
| 2006/0223055 A1 | 10/2006 | Howley et al. |
| 2007/0105839 A1 | 5/2007 | Imbach et al. |
| 2007/0179178 A1 | 8/2007 | Buettelmann et al. |
| 2007/0218135 A1 | 9/2007 | Mukharya et al. |
| 2007/0289310 A1 | 12/2007 | Dooley et al. |
| 2008/0004308 A1 | 1/2008 | Dhanak et al. |
| 2008/0081781 A1 | 4/2008 | Lippa et al. |
| 2008/0305113 A1 | 12/2008 | Kwon et al. |
| 2009/0012064 A1 | 1/2009 | Sagara et al. |
| 2009/0238828 A1 | 9/2009 | Munzert et al. |
| 2009/0260115 P1 | 11/2009 | Maier et al. |
| 2009/0281191 A1 | 11/2009 | Rangwala et al. |
| 2010/0041643 A1 | 2/2010 | Adachi et al. |
| 2010/0249412 A1 | 9/2010 | Linz et al. |
| 2010/0286127 A1 | 11/2010 | Miyoshi et al. |
| 2011/0028405 A1 | 2/2011 | Harrison et al. |
| 2011/0098288 A1 | 4/2011 | Major et al. |
| 2011/0172231 A1 | 7/2011 | Baenteli et al. |
| 2011/0201606 A1 | 8/2011 | Garcia-Echeverria et al. |
| 2011/0212077 A1 | 9/2011 | Noronha et al. |
| 2011/0245245 A1 | 10/2011 | Mortensen et al. |
| 2012/0014979 A1 | 1/2012 | Dent |
| 2012/0040961 A1 | 2/2012 | Gray et al. |
| 2012/0202798 A1 | 8/2012 | Sagara et al. |
| 2012/0329803 A1 | 12/2012 | Linz et al. |
| 2013/0184264 A1 | 7/2013 | Bradner et al. |
| 2013/0210813 A1 | 8/2013 | Bradner et al. |
| 2013/0245013 A1 | 9/2013 | Mohr et al. |
| 2013/0252331 A1 | 9/2013 | Bradner et al. |
| 2013/0261109 A1 | 10/2013 | Miyoshi et al. |
| 2013/0274239 A1 | 10/2013 | Gangloff et al. |
| 2013/0280332 A1 | 10/2013 | Moss et al. |
| 2014/0011862 A1 | 1/2014 | Bradner et al. |
| 2014/0243322 A1 | 8/2014 | Arnold et al. |
| 2015/0335656 A1 | 11/2015 | Miyoshi et al. |
| 2016/0033519 A1 | 2/2016 | Bradner et al. |
| 2016/0168154 A1 | 6/2016 | Marineau et al. |
| 2016/0231314 A1 | 8/2016 | Ryan et al. |
| 2016/0279141 A1 | 9/2016 | Bradner et al. |
| 2016/0332993 A1 | 11/2016 | Bradner et al. |
| 2016/0347749 A1 | 12/2016 | Bradner et al. |
| 2017/0008895 A1 | 1/2017 | Bradner et al. |
| 2017/0029437 A1 | 2/2017 | Bradner et al. |
| 2017/0209461 A1 | 7/2017 | Landau et al. |
| 2017/0333444 A1 | 11/2017 | Landau et al. |
| 2017/0360801 A1 | 12/2017 | Sotomayor et al. |

FOREIGN PATENT DOCUMENTS

| | | |
|---|---|---|
| CN | 101910182 A | 12/2010 |
| CN | 103037865 A | 4/2013 |
| DE | 3724164 A1 | 1/1988 |
| EP | 0 087 850 A1 | 9/1983 |
| EP | 0 368 175 A1 | 5/1990 |
| EP | 0 387 613 A1 | 9/1990 |
| EP | 0 934 940 A1 | 8/1999 |
| EP | 0 989 131 A1 | 3/2000 |
| EP | 1 297 836 A1 | 4/2003 |
| EP | 1 887 008 A1 | 2/2008 |
| EP | 2 239 264 A1 | 10/2010 |
| FR | 2329668 A1 | 5/1977 |
| JP | 61-87684 | 5/1986 |
| JP | 1-299231 | 12/1989 |
| JP | 6-157316 | 6/1994 |
| JP | H10500998 A | 1/1998 |
| JP | 11-228576 | 8/1999 |
| JP | 11-512107 | 10/1999 |
| JP | 3001979 B2 | 1/2000 |
| JP | 3096299 B2 | 10/2000 |
| JP | 2006519236 A | 8/2006 |
| JP | 2008/156311 A | 7/2008 |
| JP | 2013510123 A | 3/2013 |
| JP | 5913292 B2 | 4/2016 |
| KR | 10-2000-0016732 | 3/2000 |
| TW | 201217382 A | 5/2012 |
| WO | WO-97/13537 A1 | 4/1997 |
| WO | WO-97/37705 A1 | 10/1997 |
| WO | WO-97/47622 A1 | 12/1997 |
| WO | WO-98/11111 A1 | 3/1998 |
| WO | WO-99/34850 A1 | 7/1999 |
| WO | WO-01/95912 A1 | 12/2001 |
| WO | WO-2006/129623 A1 | 12/2006 |
| WO | WO-2007/056117 A1 | 5/2007 |
| WO | WO-2007/095188 A2 | 8/2007 |
| WO | WO-2008/063056 A2 | 7/2008 |
| WO | WO-2008/137081 A1 | 11/2008 |
| WO | WO-2009/084693 A1 | 7/2009 |
| WO | WO-2010/015387 A1 | 2/2010 |
| WO | WO-2010/049466 A1 | 5/2010 |
| WO | WO-2011/054553 A1 | 5/2011 |
| WO | WO-2011/054641 A1 | 5/2011 |
| WO | WO-2011/054644 A1 | 5/2011 |
| WO | WO-2011/054843 A1 | 5/2011 |
| WO | WO-2011/054845 A1 | 5/2011 |
| WO | WO-2011/054846 A1 | 5/2011 |
| WO | WO-2011/054848 A1 | 5/2011 |
| WO | WO-2011/143651 A1 | 11/2011 |
| WO | WO-2011/143657 A1 | 11/2011 |
| WO | WO-2011/143660 A2 | 11/2011 |
| WO | WO-2011/143669 A2 | 11/2011 |
| WO | WO-2011/161031 A1 | 12/2011 |
| WO | WO-2011/162845 A1 | 12/2011 |
| WO | WO-2012/050907 A2 | 4/2012 |
| WO | WO-2012/075383 A2 | 6/2012 |
| WO | WO-2012/075456 A1 | 6/2012 |
| WO | WO-2012/116170 A1 | 8/2012 |
| WO | WO-2012/118812 A2 | 9/2012 |
| WO | WO-2013/019710 A1 | 2/2013 |
| WO | WO-2013/030150 A | 3/2013 |
| WO | WO-2013/030450 A1 | 3/2013 |
| WO | WO-2013/033268 A2 | 3/2013 |
| WO | WO-2013/033269 A1 | 3/2013 |
| WO | WO-2013/033270 A2 | 3/2013 |
| WO | WO-2013/033420 A1 | 3/2013 |
| WO | WO-2013/097601 A1 | 7/2013 |
| WO | WO-2013/148197 A1 | 10/2013 |
| WO | WO-2013/192274 A2 | 12/2013 |
| WO | WO-2014/068402 A2 | 5/2014 |
| WO | WO-2014/071247 A1 | 5/2014 |
| WO | WO-2014/128070 A1 | 8/2014 |
| WO | WO-2014/128111 A1 | 8/2014 |
| WO | WO-2014/134583 A2 | 9/2014 |
| WO | WO-2014/144721 A2 | 9/2014 |
| WO | WO-2014/159392 A1 | 10/2014 |
| WO | WO-2014/193951 A1 | 12/2014 |
| WO | WO-2015/018521 A1 | 2/2015 |
| WO | WO-2015/018522 A1 | 2/2015 |
| WO | WO-2015/023938 A1 | 2/2015 |
| WO | WO-2015/054642 A1 | 4/2015 |
| WO | WO-2015/070020 A2 | 5/2015 |
| WO | WO-2015/081284 A1 | 6/2015 |
| WO | WO-2015/131113 A1 | 9/2015 |
| WO | WO-2016/069578 A1 | 5/2016 |
| WO | WO-2016/210275 A1 | 12/2016 |
| WO | WO-2017/059319 A2 | 4/2017 |

OTHER PUBLICATIONS

Final Rejection for U.S. Appl. No. 13/697,963, "Compositions and Methods for Modulating Metabolism," dated Jan. 18, 2017.

(56) References Cited

OTHER PUBLICATIONS

Final Rejection for U.S. Appl. No. 13/934,843, "Compositions and Methods for Treating Leukemia," dated Oct. 30, 2015.
Non-Final Rejection for U.S. Appl. No. 13/697,963, "Compositions and Methods for Modulating Metabolism," dated May 31, 2016.
Final Rejection for U.S. Appl. No. 13/934,843, "Compositions and Methods for Treating Leukemia," dated Jan. 25, 2017.
Non-Final Rejection for U.S. Appl. No. 14/977,343, "Male Contraceptive Compositions and Methods of Use," dated Aug. 24, 2016.
Non-Final Rejection for U.S. Appl. No. 15/061,576, "Compositions and Methods for Treating Neoplasia, Inflammatory Disease and Other Disorders," dated Aug. 2, 2017.
Non-Final Rejection for U.S. Appl. No. 15/121,964, "Treatment of Conditions Associated with Hyperinsulinaemia," dated Oct. 4, 2017.
Notice of Allowance for U.S. Appl. No. 14/977,343, "Male Contraceptive Compositions and Methods of Use," dated Jun. 16, 2017.
Notice of Allowance for U.S. Appl. No. 13/698,006, "Male Contraceptive Compositions and Methods of Use," dated Sep. 3, 2015.
Notice of Allowance for U.S. Appl. No. 13/934,843 dated Jul. 13, 2017.
Notice of Allowance for U.S. Appl. No. 14/977,343, "Male Contraceptive Compositions and Methods of Use," dated Feb. 13, 2017.
Notice of Allowance, U.S. Appl. No. 13/698,010, dated Aug. 21, 2014.
Notice of Allowance, U.S. Appl. No. 14/502,840, dated Dec. 4, 2015.
Office Action, U.S. Appl. No. 13/697,963, dated Nov. 21, 2014.
Office Action, U.S. Appl. No. 13/698,006, dated Apr. 10, 2014.
Office Action, U.S. Appl. No. 13/698,006, dated Oct. 23, 2014.
Office Action, U.S. Appl. No. 13/698,006, dated Sep. 26, 2013.
Office Action, U.S. Appl. No. 13/934,843, dated Mar. 23, 2015.
Requirement for Restriction/Election for U.S. Appl. No. 13/697,963, "Compositions and Methods for Modulating Metabolism," dated Mar. 20, 2014.
Requirement for Restriction/Election for U.S. Appl. No. 13/934,843, "Compositions and Methods for Treating Leukemia," dated Jul. 1, 2014.
Requirement for Restriction/Election for U.S. Appl. No. 15/034,922, "Combination Therapy for Cancer Using Bromodomain and Extra-Terminal (BET) Protein Inhibitors," dated Apr. 21, 2017.
Requirement for Restriction/Election for U.S. Appl. No. 15/061,576, "Compositions and Methods for Treating Neoplasia, Inflammatory Disease and Other Disorders," dated Feb. 15, 2017.
Abbate, et al., "Structure of the papillomavirus DNA-tethering complex E2:Brd4 and a peptide that ablates HPV chromosomal association," Mol Cell 24(6): 877-889, (2006).
Acosta et al., "Amifostine Impairs p53-mediated Apoptosis of Human Myeloid Leukemia Cells," Molecular Cancer Therapeutics, 2: 893-900 (2003).
Anders et al., "Genome-wide Localization of Small Molecules," Nat Biotechnol, 32(1): 92-96 (2014).
Arango, et al., "Reversible Azoospermia in a Patient Treated with Triazolam," Eur J Contracept Reprod Health Care, 1(3): 293-294 (1996).
Bartholomeeusen et al., "Bromodomain and Extra-terminal (BET) Bromodomain Inhibition Activate Transcription via Transient Release of Positive Transcription Elongation Factor b (P-TEFb) from 7SK Small Nuclear Ribonucleoprotein," J Biol Chem, 287(43): 36609-36619 (2012).
Baud et al., "Chemical Biology. A Bump- and-hole Approach to Engineer Controlled Selectivity of BET Bromodomain Chemical Probes," Science, 346(6209): 638-641 (2014).
Berge et al., "Pharmaceutical Salts," J Pharm Sci, 66(1): 1-19 (1977).
Berkovits, et al., "The First Bromodomain of the Testis-Specific Double Bromodomain Protein Brdt is Required for Chromocenter Organization That is Modulated by Genetic Background," Dev Biol, 360(2): 358-368 (2011).
Berkovits, et al., "The Role of the Double Bromodomain-Containing BET Genes During Mammalian Spermatogenesis," Curr Top Dev Biol, 102: 293-326 (2013).
Buchdunger, et al., "Inhibition of the Abl Protein-Tyrosine Kinase In Vitro and In Vivo by a 2-Phenylaminopyrimidine Derivative," Cancer Res, 56(1): 100-104 (1996).
Buchdunger, et al., "Selective inhibition of the platelet-derived growth factor signal transduction pathway by a protein-tyrosine kinase inhibitor of the 2-phenylaminopyrimidine class," Proc Natl Acad Sci, 92(7): 2558-2562 (1995).
Bullock, et al., "Structural basis of Inhibitor Specificity of the Human Protooncogene Proviral Insertion site in Moloney Murine ILeukemia virus (PIM-1) kinase," J Med Chem, 48(24):7604-7614 (2005).
Cellai, et al., "Mechanistic Insight Into WEB-2170-induced Apoptosis in Human Acute Myelogenous Leukemia Cells: the Crucial Role of PTEN," Exp Hematol, 37(10): 1176-1185 (2009).
Cellai, et al., "Specific PAF Antagonist WEB-2086 Induces Terminal Differentiation of Murine and Human Leukemia Cells," FASEB, 16(7): 733-735 (2002).
Chaidos et al., "Protent Antimyeloma Activity of the Novel Bromodomain Inhibitors I-BET151 and I-BET762," Blood, 123(5): 697-705 (2014).
Cheng et al., "Adjudin Disrupts Spermatogenesis via the Action of Some Unlikely Partners: Eps8, Arp2/3 complex, drebrin E, PAR6 and 14-3-3," Spermatogenesis, 1(4): 291-297 (2011).
Chesi et al., "Drug Response in a Genetically Engineered Mouse Model of Multiple Myeloma is Predictive of Clinical Efficacy," Blood, 120(2): 376-385 (2012).
Choi et al., "Brain Penetrant LRRK2 Inhibitor," ACS Med Chem Lett, 3(8): 658-662 (2012).
Cole, "Chemical probes for histone-modifying enzymes," Nat Chem Biol, 4: 590-597 (2008).
Crawford, et al., "Bromodomain 4 activation predicts breast cancer survival," Proc Natl Acad Sci, 105(17): 6380-6385 (2008).
Dawson et al., "Inhibition of BET Recruitment to Chromatin as an Effective Treatment for MLL-fusion Leukaemia," Nature, 478(7370): 529-533 (2011).
Delbroek et al., "Development of an Enzyme-linked Immunosorbent Assay for Detection of Cellular and in Vivo LRRK2 S935 Phosphorylation," J Pharm Biomed Anal, 76: 49-58 (2013).
Delmore et al., "BET Bromodomain Inhibition as a Terapeutic Strategy to Target c-Myc," cell, 146(6): 904-917 (2011).
Deng et al., "Structural Determinants for ERK5 (MAPK7) and Leucine Rich Repeat Kinase 2 Activities of Benzo[e]pyrimido-[5,4-b]diazepine-6(11H)-ones," Eur J Med Chem, 70: 758-767 (2013).
Denis, et al., "An Emerging Role for Bromodomain-Containing Proteins in Chromatin Regulation and Transcriptional Control of Adipogenesis," FEBS Lett, 584(15): 3260-3268 (2010).
Dey, et al., "Brd4 Marks Select Genes of Mitotic Chromatin and Directs Postmitotic Transcription," Mol Biol Cell, 20(23): 4899-4909 (2009).
Diamanti-Kandarakis et al., "Therapeutic Effects of Metformin on Insulin Resistance and Hyperandrogenism in Polycystic Ovary Syndrome," European Journal of Endocrinology, 138: 269-274 (1998).
Druker, et al., "Effects of a selective inhibitor of the Abl Tyrosine kinase on the Growth of Bcr-Abl positive cells," Nat Med, 2(5): 561-566 (1996).
Druker, et al., "Efficacy and safety of a specific inhibitor of the BCR-ABL tyrosine kinase in chronic myeloid leukemia," N Engl J Med, 344: 1031-1037 (2001).
Elkins et al., "X-ray Crystal Structure of ERK5 (MAPK7) in Complex with a Specific Inhibitor," J Med Chem, 56(11): 4413-4421 (2013).
Examination Report, AU Application No. 2011252808, dated Aug. 5, 2013.
Extended European Search Report for European Patent Application No. 14860080.2 dated May 3, 2017.
Extended European Search Report for PCT/US2014/048230, dated Jan. 31, 2017.

(56) References Cited

OTHER PUBLICATIONS

Fedorov, et al., "A Systematic Interaction Map of Validated Kinase Inhibitors with Ser/Thr kinases," Proc Natl Acad Sci, 104(51): 20523-20528 (2007).
Filippakopoulos et al., "Targeting Bromodomains: Epigenetic Readers of Lysine Acetylation," Nat Rev Drug Discov, 13(5): 337-356 (2014).
Filippakopoulos, et al., "Selective Inhibition of BET Bromodomains," Nature, 468(7327): 1067-1073 (2010).
French, "Demystified Molecular pathology of NUT Midline Carcinomas," J Clin Pathol, 63: 492-496 (2010).
French, et al. "BRD4-NUT Fusion Oncogene: a Novel Mechanism in Aggressive Carcinoma," Cancer Res, 63(2): 304-307 (2003).
French, et al., "BRD-NUT Oncoproteins: a Family of Closely Related Nuclear Proteins that Block Epithelial Differentiation and Maintain the Growth of Carcinoma Cells," Oncogene, 27: 2237-2242 (2008).
French, et al., "BRD4 Bromodomain Gene Rearrangement in Aggressive Carcinoma with Translocation t(15;19)," Am J Pathol, 159(6): 1987-1992 (2001).
Genbank Submission; NH/NCBI, Accession No. H86170. Hillier et al., Nov. 21, 1995. 2 pages.
Genbank Submission; NH/NCB1, Accession No. NP_001003694. Lubula et al., Oct. 6, 2016. 4 pages.
Genbank Submission; NH/NCBI, Accession No. NP_001420. Ledsaak et al., Sep. 15, 2016. 8 pages.
Genbank Submission; NH/NCBI, Accession No. NP_001717. Barda et al., Feb. 2, 2014. 2 pages.
Genbank Submission; NH/NCBI, Accession No. NP_003061. Agaimy et al., Dec. 10, 2016. 5 pages.
Genbank Submission; NH/NCBI, Accession No. NP_003063. Liao et al., May 2, 2016. 5 pages.
Genbank Submission; NH/NCBI, Accession No. NP_003843. Yuan et al., Dec. 20, 2003. 3 pages.
Genbank Submission; NH/NCBI, Accession No. NP_003875. Li et al., Oct. 7, 2016. 3 pages.
Genbank Submission; NH/NCBI, Accession No. NP_004371. Liu et al., Dec. 10, 2006. 3 pages.
Genbank Submission; NH/NCBI, Accession No. NP_004597. Herzfeld et al., Aug. 26, 2016. 5 pages.
Genbank Submission; NH/NCBI, Accession No. NP_005095. Xiao et al., Oct. 6, 2016. 4 pages.
Genbank Submission; NH/NCBI, Accession No. NP_005753. Dalgaard et al., Oct. 6, 2016. 6 pages.
Genbank Submission; NH/NCBI, Accession No. NP_009168. DiBernardo et al., Sep. 26, 2008. 2 pages.
Genbank Submission; NH/NCBI, Accession No. NP_031397. Shao et al., Jan. 4, 2017. 4 pages.
Genbank Submission; NH/NCBI, Accession No. NP_036478. Jones et al., Sep. 23, 2005. 2 pages.
Genbank Submission; NH/NCBI, Accession No. NP_054828. Hou et al., Sep. 15, 2016. 5 pages.
Genbank Submission; NH/NCBI, Accession No. NP_055392. Aberg et al., Mar. 22, 2014. 3 pages.
Genbank Submission; NH/NCBI, Accession No. NP_060404. Bezrookove et al., Oct. 7, 2016. 5 pages.
Genbank Submission; NH/NCBI, Accession No. NP_060635. Varela et al., Dec. 18, 2011. 3 pages.
Genbank Submission; NH/NCBI, Accession No. NP_060959. Kuryshev et al., Mar. 26, 2006. 2 pages.
Genbank Submission; NH/NCBI, Accession No. NP_061836. Perry et al., Feb. 21, 2016. 7 pages.
Genbank Submission; NH/NCBI, Accession No. NP_066564. Wiper-Bergeron et al., Jun. 3, 2007. 3 pages.
Genbank Submission; NH/NCBI, Accession No. NP_076413. Clark et al., Jun. 27, 2007. 2 pages.
Genbank Submission; NH/NCBI, Accession No. NP_612411. Saare et al., Aug. 25, 2016. 2 pages.
Genbank Submission; NH/NCBI, Accession No. NP_722516. Xia et al., Nov. 22, 2015. 3 pages.
Genbank Submission; NH/NCBI, Accession No. NP_872579. Lee et al., Oct. 6, 2016. 4 pages.
Genbank Submission; NH/NCBI, Accession No. XP_039676. Aug. 19, 2004. 3 pages.
Greenwald, et al., "Eμ-BRD2 Transgenic Mice Develop B-Cell Lymphoma and Leukemia," Blood, 103(4): 1475-1484 (2004).
Haack, et al., "Diagnosis of NUT Midline Carcinoma Using a NUT-specific Monoclonal Antibody," Am J Surg Pathol, 33(7): 984-991 (2009).
He et al., "The Histone Methyltransferase Ezh2 is a Crucial Epigenetic Regulator of Allogeneic T-cell Responses Mediating Graft-versus-host Disease," Blood, 122(25): 119-128 (2013).
Hedrington et al., "Effects of Antecedent GABAA Activation with Alprazolam on Counterregulatory Responses to Hypoglycemia in Healthy Humans," Diabetes, 59(4): 1074-1081 (2010).
Houzelstein et al., "Growth and Early Postimplantation Defects in Mice Deficient for the Bromodomain-containing Protein Brd4," Mol Cell Biol, 22(11): 3794-3602 (2002).
Hsu et al., "Metabolic Syndrome, Hyperinsulinemia and Cancer," The American Journal of Clinical Nutrition, 86(3): 867S-871S (2007).
Hu, et al., "Adjudin Targeting Rabbit Germ Cell Adhesion as a Male Contraceptive: A Pharmacokinetics Study," J Androl, 30(1): 87-93 (2009).
Huang, et al., "Brd4 Coactivates Transcriptional Activation of NF-κB via Specific Binding to Acetylated ReIA," Mol Cell Biol, 29(5): 1375-1387 (2009).
International Preliminary Report for International Application No. PCT/US14/64549 dated May 10, 2016.
International Preliminary Report on Patentability for International Application No. PCT/US2015/018118 dated Sep. 6, 2016.
International Preliminary Report on Patentability for International Application No. PCT/US2015/057538 dated May 2, 2017.
International Preliminary Report on Patentability for PCT/US2014/023386, dated Sep. 24, 2015.
International Preliminary Report on Patentability for PCT/US2014/48230, dated Feb. 4, 2016.
International Preliminary Report on Patentability for PCT/US2015/044180, dated Feb. 23, 2017.
International Preliminary Report on Patentability for PCT/US2015/044303, dated Feb. 23, 2017.
International Preliminary Report on Patentability for PCT/US2015/14039, dated Aug. 11, 2016.
International Preliminary Report on Patentability for PCT/US2015/14044, dated Aug. 11, 2016.
International Preliminary Report on Patentability for PCT/US2015/14109, dated Aug. 11, 2016.
International Preliminary Report on Patentability for PCT/US2015/14120, dated Aug. 11, 2016.
International Search Report and Written Opinion for International Application No. PCT/US14/64549 dated Mar. 11, 2015.
International Search Report and Written Opinion for International Application No. PCT/US2015/018118 dated May 19, 2015.
International Search Report and Written Opinion for International Application No. PCT/US2015/057538 dated Jan. 21, 2016.
International Search Report and Written Opinion for International Application No. PCT/US2016/054924 dated Sep. 5, 2017.
International Search Report and Written Opinion for PCT/US2014/023386, dated Jul. 9, 2014.
International Search Report and Written Opinion for PCT/US2014/14120, dated Apr. 23, 2015.
International Search Report and Written Opinion for PCT/US2014/48230, dated Jan. 30, 2015.
International Search Report and Written Opinion for PCT/US2015/044180, dated Nov. 5, 2015.
International Search Report and Written Opinion for PCT/US2015/044303, dated Dec. 31, 2015.
International Search Report and Written Opinion for PCT/US2015/059551, dated Jan. 13, 2016.
International Search Report and Written Opinion for PCT/US2015/059622, dated Mar. 30, 2016.
International Search Report and Written Opinion for PCT/US2015/14039, dated Apr. 23, 2015.

(56) References Cited

OTHER PUBLICATIONS

International Search Report and Written Opinion for PCT/US2015/14044, dated Apr. 23, 2015.
International Search Report and Written Opinion for PCT/US2015/14109, dated Jul. 6, 2015.
International Search Report and Written Opinion for PCT/US2016/051017, dated Jan. 10, 2017.
International Search Report and Written Opinion for PCT/US2016/051107, dated Nov. 22, 2016.
Kadota, et al. "Identification of Novel Gene Amplifications in Breast Cancer and Coexistence of Gene Amplification With an Activating Mutation of PIK3CA," Cancer Res, 69(18): 7357-7365 (2009).
Kavanagh et al., "The Development of CNS-active LRRK2 Inhibitors Using Property-directed Optimisation," Bioorg Med Chem Lett, 23(13): 3690-3696 (2013).
Kim, et al., "Berberine Improves Lipid Dysregulation in Obesity by Controlling Central and Peripheral AMPK Activity," Am J Physiol Endocrinol Metab, 296(4): E812-E819 (2009).
Konze et al., "An Orally Bioavailable Chemical Probe of the Lysine Methyltransferases EZH2 and EZH1," ACS Chem Biol, 8(6): 1324-1334 (2013).
Krueger et al., "The Mechanism of Release of P-TEFb and HEXIM1 from the 7SK snRNP by Viral and Cellular Activators Includes a Conformational change in 7SK," PLoS One, 5(8): e12335 (2010).
Lawless, et al., "Histone Deacetylase Inhibitors Target Diabetes Via Chromatin Remodeling or as Chemical Chaperones?" Curr Diabetes Rev, 5(3): 201-209 (2009).
Le Coutre, et al., "In vivo eradication of human BCR/ABL-positive leukemia cells with an ABL kinase inhibitor," J Natl Cancer Inst, 91(2): 163-168 (1999).
Lee et al., "Synergistic Effect of JG1 and Rapamycin for Treatment of Human Osteosarcoma," Int J Cancer, 136(9): 2055-2064 (2014).
Lee, et al., "Berberine, a Natural Plant Product, Activates AMP-Activated Protein Kinase with Beneficial Metabolic Effects in Diabetic and Insulin-Resistant States," Diabetes, 55(8): 2256-2264 (2006).
Lotti et al., "Ultrasound of the Male Genital Tract in Relation to Male Reproductive Health," Hum Reprod Update, 21(1): 56-83 (2015).
Marushige, "Activation of Chromatin by Acetylation of Histone Side Chains," Proc Natl Acad Sci, 73(11): 3937-3941 (1976).
Matzuk, et al., "Small-Molecule Inhibition of BRDT for Male Contraception," Cell, 150(4): 673-684 (2012).
McKeown et al., "Biased Multicomponent Reactions to Develop Novel Bromodomain Inhibitors," J Med Chem, 57(21): 9019-9027 (2014).
Meguro, et al., "Heterocycles. VI.1) Synthesis of 4H-s-Triazolo[4,3-α][1,4]benzodiazepines, Novel Tricyclic Psychosedatives," Chem Pharm Bull, 21(11): 2382-2390 (1973).
Meng-er, et al., "Use of All-Trans Retinoic Acid in the Treatment of Acute Promyelocytic Leukemia," Blood, 72(2): 567-572 (1988).
Mochizuki, et al., "The Bromodomain Protein Brd4 Stimulates G1 Gene Transcription and Promotes Progression to S Phase," J Biol Chem, 283(14): 9040-9048 (2008).
Moros et al., "Synergistic Anti-tumor Activity of Lenalidomide with the BET Bromodomain Inhibitor CPI203 in Borlezomib-resistant Mantle Cell Lymphoma," Leukemia 28(10): 2049-2059 (2014).
Niesen, et al., "The use of Differential Scanning Fluorimetry to Detect Ligand Interactions that Promote Protein Stability," Nat Protoc, 2(9): 2212-2221 (2007).
Nishimura et al., "Fertility and Reproduction Studies of Apafant (WEB 2086 BS) in Rats Dosed Orally," Oyo Yakuri/Pharmacometrics, 52(3/4): 185-200 (1996).
Notification Concerning Transmittal of International Preliminary Report on Patentability, International Application No. PCT/US2011/036647, Titled: "Compositions and Methods of Modulating Metabolism", dated Nov. 29, 2012.
Notification Concerning Transmittal of International Preliminary Report on Patentability, International Application No. PCT/US2011/036667, Titled: "Male Contraceptive Compositions and Methods of Use", dated Nov. 29, 2012.
Notification Concerning Transmittal of International Preliminary Report on Patentability, International Application No. PCT/US2011/036672, Titled: "Compositions and Methods for Treating Leukemia", dated Nov. 29, 2012.
Notification Concerning Transmittal of International Preliminary Report on Patentability, International Application No. PCT/US2011/036701, Titled: "Compositions and Methods for Treating Neoplasia, Inflammatory Disease and Other Disorders", dated Nov. 29, 2012.
Notification of Transmittal of the International Search Report and the Written Opinion of the International Searching Authority, International Application No. PCT/US11/36647, Titled: "Compositions and Methods of Modulating Metabolism", dated Aug. 17, 2011.
Notification of Transmittal of the International Search Report and the Written Opinion of the International Searching Authority, International Application No. PCT/US11/36667, Titled: "Male Contraceptive Compositions and Methods of Use", dated Aug. 15, 2011.
Notification of Transmittal of the International Search Report and the Written Opinion of the International Searching Authority, International Application No. PCT/US11/36672, Titled: "Compositions and Methods for Treating Leukemia", dated Jan. 27, 2012.
Notification of Transmittal of the International Search Report and the Written Opinion of the International Searching Authority, International Application No. PCT/US11/36701, Titled: "Compositions and Methods for Treating Neoplasia, Inflammatory Disease and Other Disorders", dated Feb. 1, 2012.
Owen, et al., "The Structural Basis for the Recognition of Acetylated Histone R4 by the Bromodomain of Histone Acetyltransferase Gcn5p," The EMBO Journal, 19(22): 6141-6149 (2000).
Patani, et al., "Bioisosterism: A Rational Approach in Drug Design," Chem Rev, 96(8): 3147-3176 (1996).
Phelps, et al., "Clinical Response and Pharmacokinetics from a Phase 1 Study of an Active Dosing Schedule of Flavopiridol in Relapsed Chronic Lymphocytic Leukemia," Blood, 113(12): 2637-2645 (2009).
Preisler, et al., "Assessment of c-myc Expression in Individual Leukemic Cells," Leuk Res, 12(6): 507-516 (1988).
Ptashne, "Binding Reactions: Epigenetic Switches, Signal Transduction and Cancer," Curr Biol, 19(6): R234-R241 (2009).
PubChem CID 5325760. Published Jan. 25, 2006.
PubChem CID-55504609. Created Jan. 25, 2012.
PubChem CID-56267130. Created Jan. 25, 2012.
PubChem SID 225027960. Available date/deposit date: Feb. 2, 2015.
PubChem SID 235048169. Feb. 13, 2015.
PubChem SID 235671906. Feb. 12, 2015.
Quinn, et al., "A homogeneous method for investigation of methylation-dependent protein-protein interactions in epigenetics," Nucleic Acids Res, 38(2): e11(1-10) (2010).
Rahl, et al., "c-Myc Regulates Transcriptional Pause Release," Cell, 141(3): 432-445 (2010).
Roberts et al., "A Bead-Based Proximity Assay for BRD4 Ligand Discovery," Curr Protoc Chem Biol, 7(4): 263-278 (2015).
Santillan, et al., "Bromodomain and Histone Acetyltransferase Domain Specificities Control Mixed Lineage Leukemia Phenotype," Cancer Res, 66(20): 10032-10039 (2006).
Schindler, et al. "Structural mechanism for STI-571 Inhibition of Abelson Tyrosine kinase. Science," 289(5486): 1938-1942 (2000).
Schreiber, et al., "Signaling Network Model of Chromatin," Cell, 111(6): 771-778 (2002).
Schroder et al., "Two-pronged Binding with Bromodomain-containing Protein 4 Liberates Positive Transcription Elongation Factor B from Inactive Ribonucleoprotein Complexes," J Biol Chem, 287(2): 1090-1099 (2012).
Seyrig, et al., "Effects of a Chronic Administration of Two Benzodiazepines on Food Intake in Rats Given a Highly Palatable Diet," Pharmacology Biochemistry & Behavior, 25(4): 913-918 (1986).
Shang, et al., "The First Bromodomain of Brdt, a Testis-Specific Member of the BET Sub-Family of Double-Bromodomain-

(56) References Cited

OTHER PUBLICATIONS

Containing Proteins, is Essential for Male Germ Cell Differentiation," Development, 134: 3507-3515 (2007).
Smith et al., "The Bromodomain: A New Target in Emerging Epigenetic Medicine," ACS Chem Biol, 11(3): 598-608 (2016).
Tanaka et al., "Inhibitors of Emerging Epigenetic Targets for Cancer Therapy: A Patient Review (2010-2014)," Pharm Pat Anal, 4(4): 261-284 (2015).
Taskinen, et al., "A High Tumor-Associated Macrophage Content Predicts Favorable Outcome in Follicular Lymphoma Patients Treated with Rituximab and Cyclophosphamide-Doxorubicin-Vincristine-Prednisone," Clin Cancer Res, 13(19): 5784-5785 (2007).
Tse et al., "ABT-263: A Potent and Orally Bioavaliable Bcl-2 Family Inhibitor," Cancer Res, 68(9): 3421-3428 (2008).
Verma et al., "Identification of Potent, Selective, Cell-Active Inhibitors of the Histone Lysine Methyltransferase EZH2," ACS Med Chem Lett, 3(12): 1091-1096 (2012).
Vollmuth, et al., "Structures of the dual bromodomains of the P-TEFb-activating protein Brd4 at atomic resolution," J Biol Chem, 284(52): 36547-36556 (2009).
VonVoigtlander, et al., "Alprazolam: Review of Pharmacological, Pharmacokinetic and Clinical Data," Drug Dev Res, 6(1): 1-12 (1985).
Wang, et al., "A Seamless Trespass: Germ Cell Migration Across the Seminiferous Epithelium During Spermatogenesis," J Cell Biol, 178(4): 549-556 (2007).
Wang, et al., "Brd2 Disruption in Mice Causes Severe Obesity Without Type 2 Diabetes," Biochem J, 425(1): 71-83 (2010).
Wehner et al., "Effects of Natlizumab, an Alpha4 Integrin Inhibitor, on Fertility in Male and Female Guinea Pigs," Birth Defects Res B Dev Reprod Toxicol, 86(2): 108-116 (2009).
Yang, "Multisite Protein Modification and Intramolecular Signaling," Oncogene, 24: 1653-1662 (2005).
Yang, et al., "AZD1152, a novel and selective aurora B kinase inhibitor, induces growth arrest, apoptosis, and sensitization for tubulin depolymerizing agent or topoisomerase II inhibitor in human acute leukemia cells in vitro and in vivo," Blood, 110(6): 2034-2040 (2007).
Yang, et al., "Brd4 recruits P-TEFb to chromosomes at late mitosis to promote G1 gene expression and cell cycle progression," Mol Cell Biol, 28(3): 967-976 (2008).
Yang, et al., "Recruitment of P-TEFb for Stimulation of Transcriptional Elongation by the Bromodomain Protein Brd4," Mol Cell, 16(4): 535-545 (2005).
You, et al., "Kaposi's sarcoma-associated herpesvirus latency-associated nuclear antigen interacts with bromodomain protein Brd4 on host mitotic chromosomes," J Virol, 80(18): 8909-8919 (2006).
You, et al., "Regulation of Aurora B Expression by the Bromodomain Protein Brd4," Mol Cell Biol, 29: 5094-5103 (2009).
Zeng, et al., "Bromodomain: an Acetyl-lysine Binding Domain," FEBS Lett, 513(1): 124-128 (2002).
Zhang, et al., "Down-Regulation of NF-κB Transcriptional Activity in HIV-Associated Kidney Disease by BRD4 Inhibition," J Biol Chem, 287(34): 28840-28851 (2012).
Zhang, et al., "Down-Regulation of NF-κB Transcriptional Activity in HIV-Associated Kidney Disease by BRD4 Inhibition," J Biol Chem, 287(46): 38956 (2012).
Zhao, et al., "Research Development on Fusion Protein Transcription Factor siRNA Specifically Targeting Leukemia," Sciencepaper Online: 1-6 and J Med Res, 39(2): 6-9 (2010) (English-language translation entitled "Progress of Research on siRNA that Targets Leukemia Specific Transcription Regulation Factor Fusion Proteins," 1-10).
Zuber, et al., "RNAi Screen Identifies Brd4 as a Therapeutic Target in Acute Myeloid Leukaemia," Nature, 478(7370): 524-528 (2011), with "Supplementary Information" from www.nature.com/nature/journal/v478/n7370/extref/nature10334-s1.pdf, pp. 1-33.
Zuercher et al., "Identification and Structure-activity Relationship of Phenolic Acyl Hydrazones as Selective Agonists for the Estrogen-related Orphan Nuclear Receptors ERRbeta and ERRgamma," J Med Chem, 48(9): 107-109 (2005).
Non-Final Rejection for U.S. Appl. No. 15/034,922, "Combination Therapy for Cancer Using Bromodomain and Extra-Terminal (Bet) Protein Inhibitors," dated Mar. 8, 2018.
Office Action, U.S. Appl. No. 15/522,222, dated Mar. 2, 2018.
International Preliminary Report on Patentability for International Application No. PCT/US2016/039270 dated Dec. 26, 2017.
International Search Report and Written Opinion for International Application No. PCT/US2016/039270 dated Oct. 18, 2016.
Mertz et al., "Targeting MYC Dependence in Cancer by Inhibiting BET Bromodomains," PNAS, 108(40): 16669-16674 (2011).
Rhein et al., "CD11b is a Therapy Resistance and Minimal Residual Disease-Specific Marker in Precursor B-cell Acute Lymphoblastic Leukemia," Blood, 115(18): 3763-3771 (2010).
Souers et al., "ABT-199, a Potent and Selective BCL-2 Inhibitor, Achieves Antitumor Activity While Sparing Platelets," Nature Medicine, 19(2): 202-210 (2013).
Wang et al., "Activation of SOX2 Expression BRD4-NUT Oncogenic Fusion Drives Neoplastic Transformation in NUT Midline Carcinoma," Cancer Research, 74(12): 3332-3343 (2014).
Wass et al., "Crizotinib in ALK-Positive Diffuse Large B-Cell Lymphoma: A Case Report," Blood, 120(21): 4862 (2012).

BROMODOMAIN INHIBITORS

RELATED APPLICATIONS

This application is the U.S. National Stage of International Application No. PCT/US2015/057538, filed Oct. 27, 2015, which designates the U.S., published in English, which claims the benefit of U.S. Provisional Application No. 62/068,983, filed on Oct. 27, 2014. The entire teaching of the above application is incorporated herein by reference.

BACKGROUND OF THE INVENTION

Histone N-terminal tails maintain chromatin stability and are subject to modifications associated with transcriptional regulation. The best characterized of these modifications are acetylation, methylation and phosphorylation For each modification, enzymes exist that either lay down the appropriate mark or remove it. These modifications must then be interpreted by the transcriptional machinery. Acetyl-lysine recognition is principally mediated by bromodomains, which are commonly components of transcription factor complexes. The bromodomain and extra-terminal (BET)-family (e.g., BRD2, BRD3, BRD4 and BRDT) share a common domain architecture comprising two N-terminal bromodomains which exhibit a high level of sequence conservation, and a more divergent C-terminal domain which is implicated in protein-protein interactions. Aberrant regulation of histone modification can impact gene activity and play a role in oncogenesis. Lysine sidechain acetylation is an important regulatory event in the function of non-histone proteins, including but not limited to Hsp90, p53, STAT transcription factors, cortactin, beta-catenin and alpha-tubulin. Thus, modulation of lysine sidechain recognition would be expected to exert important phenotypic and therapeutic effects broadly in development and disease. Despite the importance of acetyl-lysine recognition to oncogenesis, few modulators of acetyl-lysine recognition have been identified.

SUMMARY OF THE INVENTION

As described below, the present invention features compositions and methods of treating a disorder responsive to the modulation of a BET family polypeptide. In a particular embodiment, the disorder responsive to the modulation of a BET family member includes a neoplasia, inflammatory disease, hyperinsulinaemia (e.g., insulinoma, congenital hyperinsulism, polycystic ovary syndrome (PCOS), Beckwith-Wiedemann syndrome and in patients following gastric bypass surgery), obesity, fatty liver (NASH or otherwise), diabetes, atherosclerosis, arterial stent occlusion, heart failure, cachexia, graft versus host disease, infectious diseases associated with bromodomains, the treatment of parasites, malaria, trypanosomes, and for reducing male fertility. Further uses of the compositions of the invention include, but are not limited to, use in organ transplantation, modulation of cell state for regenerative medicine (i.e., by promoting or inhibiting cellular differentiation), and facilitating pluripotency. More specifically, the invention provides compositions and methods of treating a disorder responsive to the modulation of a BET family polypeptide comprising a bromodomain with acetyl-lysine and/or chromatin (e.g., disrupting a bromodomain interaction with an acetyl-lysine modification present on a histone N-terminal tail).

In one aspect, the invention provides a compound of Structural Formula I:

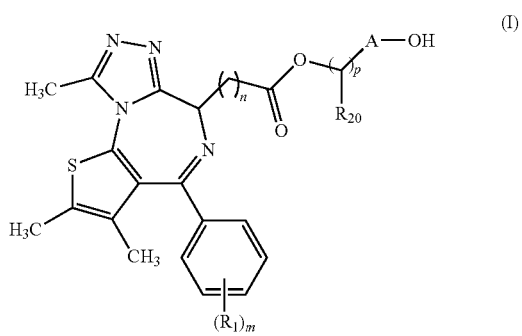

or a pharmaceutically acceptable salt thereof, wherein:
A is selected from the group consisting of a $(C_1-C_6)$alkyl, a $(C_2-C_6)$alkenyl, a $(C_2-C_6)$alkynyl, a $(C_3-C_{12})$cycloalkyl, and a $(C_5-C_7)$heterocycloalkyl, wherein moiety A is optionally substituted with 1 to 4 $R_2$ groups;
$R_{20}$ for each occurence independently, is —H, —OH, a $(C_1-C_3)$ alkyl, a $(C_3-C_{12})$cycloalkyl, or a $(C_5-C_7)$heterocycloalkyl;
$R_1$ for each occurence independently is selected from the group consisting of —OH, a halogen, —CN, a $(C_1-C_4)$ alkoxy, —C(O)($C_1-C_4$)alkyl, —C(O)O($C_1-C_4$)alkyl, —OC(O)($C_1-C_4$ alkyl), —C(O)$NR_3R_4$, —$NR_5C(=O)R_6$, a $(C_1-C_6)$alkyl, a $(C_2-C_6)$alkenyl, a $(C_3-C_2)$cycloalkyl, and a $(C_5-C_7)$heterocycloalkyl;
$R_2$ for each occurence independently is a $(C_1-C_6)$alkyl, a $(C_2-C_6)$alkenyl, a halo($C_1-C_6$)alkoxy, a halo($C_1-C_6$)alkyl, a hydroxy($C_1-C_6$)alkyl, a $(C_1-C_6)$alkoxy($C_1-C_6$)alkyl, a $(C_3-C_{12})$ cycloalkyl, a —($C_1-C_6$)alkylene-($C_3-C_{12}$)cycloalkyl, a $(C_3-C_{12})$ heterocycloalkyl, a —($C_1-C_6$)alkylene-($C_3-C_2$)heterocycloalkyl, a $(C_1-C_6)$alkoxy, —C(O)($C_1-C_6$ alkyl), —C(O)O($C_1-C_6$ alkyl), —OC(O)($C_1-C_6$ alkyl), —C(O)$NR_7R_8$, —$NR_9C(=O)R_{10}$, —$NR_{11}R_{12}$, a halogen, an oxo, or —OH;
$R_3, R_4, R_5, R_6, R_7, R_8, R_9, R_{10}, R_{11}$, and $R_{12}$ are each independently H or a $(C_1-C_4)$alkyl; and
each m, n and p is independently 0, 1, 2, 3, or 4.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Definitions

Figure 1:
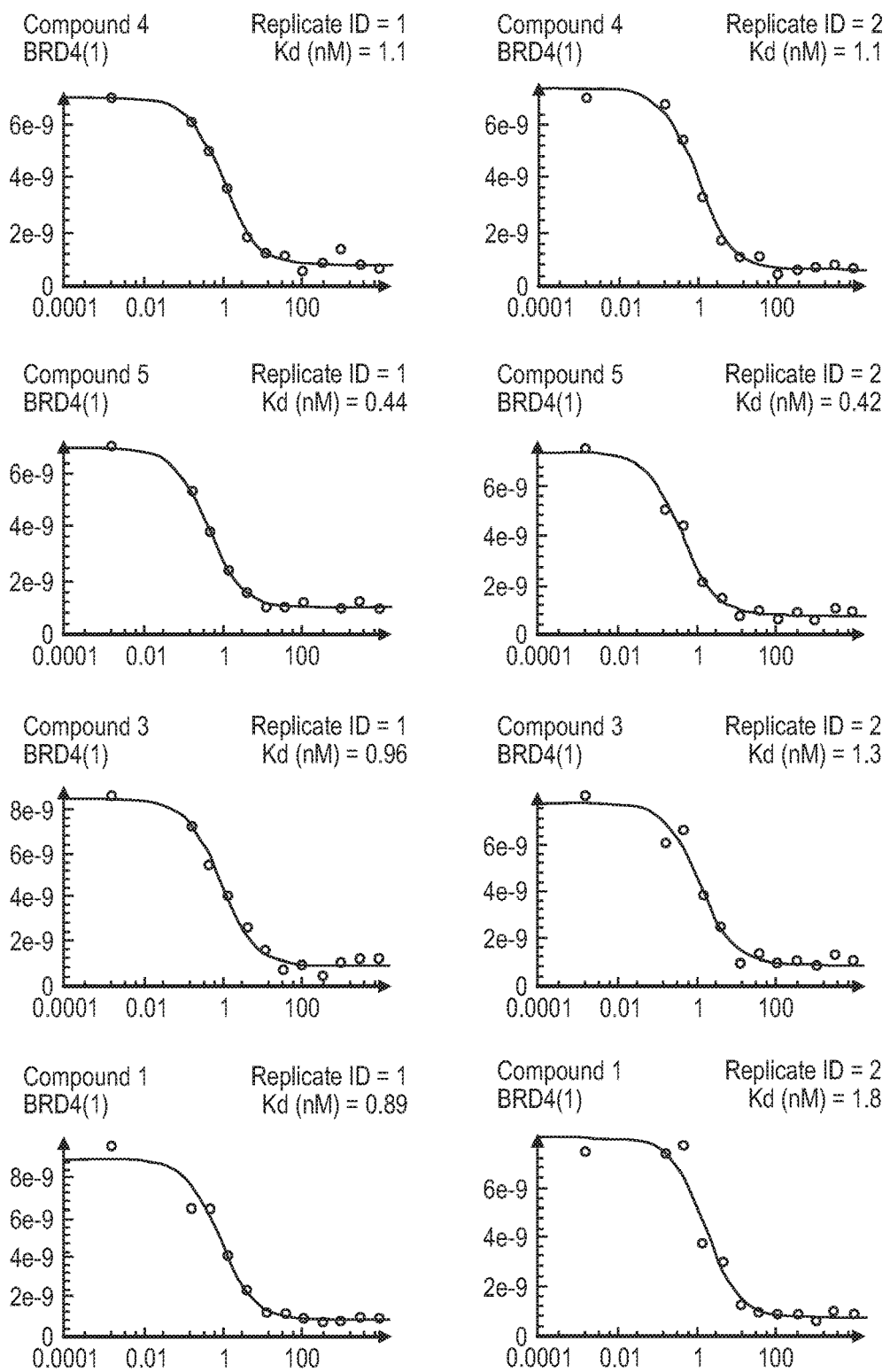
FIG. 1 shows graphs of the BRD4(1) binding activity of Compounds 1, 3, 4 and 5.

"Alkyl" means an optionally substituted saturated aliphatic branched or straight-chain monovalent hydrocarbon radical having the specified number of carbon atoms. Thus, "$(C_1-C_6)$ alkyl" means a radical having from 1-6 carbon atoms in a linear or branched arrangement. "$(C_1-C_6)$alkyl" includes methyl, ethyl, propyl, iso-propyl (or i-propyl), butyl, sec-butyl, tert-butyl, pentyl, hexyl and the like. The terms "alkyl", "alkoxy", "hydroxyalkyl", "haloalkyl", "aralkyl", "alkoxyalkyl", "alkylamine", "dialkylamine", "alkylamino", "dialkylamino", "alkoxycarbonyl" and the like, used alone or as part of a larger moiety includes both straight and branched saturated chains containing one to twelve carbon atoms.

"Alkylene" means an optionally substituted saturated aliphatic branched or straight-chain divalent hydrocarbon radical having the specified number of carbon atoms. Thus, "$(C_1-C_6)$alkylene" means a divalent saturated aliphatic radical having from 1-6 carbon atoms in a linear arrangement, e.g., $-[(CH_2)_n]-$, where n is an integer from 1 to 6, "$(C_1-C_6)$alkylene" includes methylene, ethylene, propylene, butylene, pentylene and hexylene. Alternatively, "$(C_1-C_6)$alkylene" means a divalent saturated radical having from 1-6 carbon atoms in a branched arrangement, for example: $-[(CH_2CH_2CH_2CH_2CH(CH_3))]-$, $-[(CH_2CH_2C_2CH_2CH_2C(CH_3)_2]-$, $-[(CH_2C(CH_3)_2CH(CH_3))]-$, and the like. A specific branched $C_3$-alkylene is

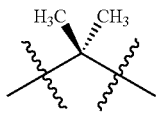

and a specific $C_4$-alkylene is

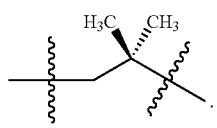

Each alkyl or alkylene in Structural Formulas (I-II) can be optionally and independently substituted with one or more substituents.

"Alkenyl" means branched or straight-chain monovalent hydrocarbon radical containing at least one double bond and having specified number of carbon atoms. Alkenyl may be mono or polyunsaturated, and may exist in the E or Z onfiguration. For example, "$(C_2-C_6)$alkenyl" means a radical having from 2-6 carbon atoms in a linear or branched arrangement.

"Alkynyl" means branched or straight-chain monovalent hydrocarbon radical containing at least one triple bond and having specified number of carbon atoms. For example, "$(C_2-C_6)$alkynyl" means a radical having from 2-6 carbon atoms in a linear or branched arrangement.

By "bromodomain" is meant a portion of a polypeptide that recognizes acetylated lysine residues. In one embodiment, a bromodomain of a BET family member polypeptide comprises approximately 110 amino acids and shares a conserved fold comprising a left-handed bundle of four alpha helices linked by diverse loop regions that interact with chromatin.

By "BET family polypeptide" is meant a polypeptide comprising two bromodomains and an extraterminal (ET) domain or a fragment thereof having transcriptional regulatory activity or acetylated lysine binding activity. Exemplary BET family members include BRD2, BRD3, BRD4 and BRDT.

"Cycloalkyl" means a saturated aliphatic cyclic hydrocarbon ring. "Cycloalkyl" includes 3- to 12-membered saturated aliphatic cyclic hydrocarbon rings. Thus, "$(C_3-C_7)$ cycloalkyl" means a hydrocarbon radical of a 3- to 7-membered saturated aliphatic cyclic hydrocarbon ring. A $(C_3-C_7)$cycloalkyl includes, but is not limited to cyclopropyl, cyclobutyl, cyclopentyl, cyclohexyl and cycloheptyl.

A cycloalkyl moiety can be monocyclic, fused bicyclic, bridged bicyclic, spiro bicyclic, or polycyclic. For example, monocyclic $(C_3-C_8)$cycloalkyl means a radical having from 3 to 8 carbon atoms arranged in a monocyclic ring. Monocyclic $(C_3-C_8)$cycloalkyl includes, but is not limited to, cyclopropyl, cyclobutyl, cyclopentyl, cyclohexyl, cycloheptyl and cyclooctane.

Monocyclic ring systems have a single ring structure. They include saturated or unsaturated aliphatic cyclic hydrocarbon rings (e.g., cycloalkyl, cycloalkenyl, or cycloalkynyl) or aromatic hydrocarbon rings (e.g., aryl) having the specified number of carbon atoms. The monocyclic ring system can optionally contain 1 to 5 heteroatoms in the ring structure wherein each heteroatom is independently selected from the group consisting O, N and S (e.g., heterocycloalkyl, heterocycloalkenyl, heterocycloalkynyl or heteroaryl). When the heteroatom is N, it can be optionally substituted with alkyl, cycloalkyl, alkylene-cycloalkyl, heterocycloalkyl, alkylene-heterocycloalkyl, aryl, alkylene-aryl, heteroaryl, alkylene-heteroaryl, each of which can be optionally substituted with one or more halogen, =O, hydroxy, alkoxy, haloalkyl, alkyl, etc. When the heteroatom is S, it can be optionally mono- or di-oxygenated (i.e., $-S(O)-$ or $-S(O)_2-$). Examples of monocyclic ring systems include, but are not limited to, cyclopropyl, cyclobutyl, cyclopentyl, cyclohexyl, cycloheptyl, cyclooctane, azetidine, pyrrolidine, piperidine, piperazine, azepane hexahydropyrimidine, tetrahydrofuran, tetrahydropyran, oxepane, tetrahydrothiophene, tetrahydrothiopyran, isoxazolidine, 1,3-dioxolane, 1,3-dithiolane, 1,3-ioxane, 1,4-dioxane, 1,3-dithiane, 1,4-dithiane, morpholine, thiomorpholine, thiomorpholine 1,1-dioxide, tetrahydro-2H-1,2-thiazine, tetrahydro-2H-1,2-thiazine 1,1- dioxide, and isothiazolidine 1,1-dioxide, tetrahydrothiophene 1-oxide, tetrahydrothiophene 1,1-dioxide, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one.

Bicyclic ring systems have two rings that have at least one ring atom in common. Bicyclic ring systems include fused, bridged and spiro ring systems. The two rings can both be aliphatic (e.g., cycloalkyl, cycloalkene, cycloalkyne, or heterocycloalkyl), both be aromatic (e.g., aryl or heteroaryl), or a combination thereof. The bicyclic ring systems can optionally contain 1 to 5 heteroatoms in the ring structure wherein each heteroatom is independently selected from the group consisting O, N and S. When the heteroatom is N, it can be substituted with H, alkyl, cycloalkyl, alkylene-cycloalkyl, heterocycloalkyl, alkylene-heterocycloalkyl, aryl, alkylene-aryl, heteroaryl, alkylene-heteroaryl, each of which can be optionally substituted with one or more halogen, =O, hydroxy, alkoxy, haloalkyl, alkyl, etc. When the heteroatom is S, it can be optionally mono- or di-oxygenated (i.e. —S(O)— or —S(O)$_2$).

A fused bicyclic ring system has two rings which have two adjacent ring atoms in common. The two rings can both be aliphatic (e.g., cycloalkyl, cycloalkene, cycloalkyne, or heterocycloalkyl), both be aromatic (e.g., aryl or heteroaryl), or a combination thereof. For example, the first ring can be cycloalkyl or heterocycloalkyl, and the second ring can be a cycloalkyl, cycloalkene, cycloalkyne, aryl, heteroaryl or a heterocycloalkyl. For example, the second ring can be a (C$_3$-C$_6$)cycloalkyl, such as cyclopropyl, cyclobutyl, cyclopentyl and cyclohexyl. Alternatively, the second ring can be an aryl ring (e.g., phenyl). Examples of fused bicyclic ring systems include, but are not limited to, 6,7,8,9-tetrahydro-5H-benzo[7]annulene, 2,3-dihydro-H-indene, octahydro-1H-indene, tetrahydronaphthalene, decahydronaphthalene, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, 3-azabicyclo[3.2.0]heptane, 5,6,7,8-tetrahydroquinoline and 5,6,7,8-tetrahydroisoquinoline, and 2,3,4,5-tetrahydrobenzo[b]oxepine.

A spiro bicyclic ring system has two rings which have only one ring atom in common. The two rings can both be aliphatic (e.g., cycloalkyl, cycloalkene, cycloalkyne, or heterocycloalkyl), both be aromatic (e.g., aryl or heteroaryl), or a combination thereof. For example, the first ring can be a cycloalkyl or a heterocycloalkyl and the second ring can be a cycloalkyl, a cycloalkene, a cycloalkyne, an aryl, a heteroaryl, or a heterocycloalkyl. Examples of spiral bicyclic ring systems include, but are not limited to, spiro[2.2]pentane, spiro[2.3]hexane, spiro[3.3]heptane, spiro[2.4]heptane, spiro[3.4]octane, spiro[2.5]octane, azaspiro[4.4]nonane, 7-azaspiro[4.4]nonane, azaspiro[4.5]decane, 8-azaspiro[4.5]decane, azaspiro[5.5]undecane, 3-azaspiro[5.5]undecane, and 3,9-diazaspiro[5.5]undecane.

A bridged bicyclic ring system has two rings which have three or more adjacent ring atoms in common. The two rings can both be aliphatic (e.g., cycloalkyl, cycloalkene, cycloalkyne, or heterocycloalkyl), both be aromatic (e.g., aryl or heteroaryl), or a combination thereof. For example, the first ring can be a cycloalkyl or a heterocycloalkyl and the other ring is a cycloalkyl, a cycloalkene, a cycloalkyne, an aryl, a heteroaryl or a heterocycloalkyl. Examples of bridged bicyclic ring systems include, but are not limited to, bicyclo[1.1.0]butane, bicyclo[1.2.0]pentane, bicyclo[2.2.0]hexane, bicyclo[3.2.0]heptane, bicyclo[3.3.0]octane, bicyclo[4.2.0]octane, bicyclo[2.2.1]heptane, bicyclo[2.2.2]octane, bicyclo[3.2.1]octane, bicyclo[3.2.2]nonane, bicyclo[3.3.1]nonane, bicyclo[3.3.2]decane bicyclo[3.3.3]undecane, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane, and 2-oxabicyclo[2.2.2]octane.

Polycyclic ring systems have more than two rings (e.g., three rings resulting in a tricyclic ring system) and adjacent rings have at least one ring atom in common. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common. Examples of polycyclic ring systems include, but are not limited to, tricyclo[3.3.1.0$^{3,7}$]nonane (noradamantane), tricyclo[3.3.1.1$^{3,7}$]decane (adamantane) and 2,3-dihydro-1H-phenalene.

"Alkoxy" refers to the group —O—R where R is "alkyl", "cycloalkyl", "alkenyl", or "alkynyl". "(C$_1$-C$_6$)alkoxy" includes methoxy, ethoxy, ethenoxy, propoxy, butoxy, pentoxy, and the like.

"Hydroxyalkyl" and "alkoxyalkyl" are alkyl groups substituted with hydroxyl and alkoxy, respectively.

"Amino" means —NH$_2$; "alkylamine" and "dialkylamine" mean —NHR and —NR$_2$, respectively, wherein R is an alkyl group. "Cycloalkylamine" and "dicycloalkylamine" mean —NHR and —NR$_2$, respectively, wherein R is a cycloalkyl group. "Cycloalkylalkylamine" means —NHR wherein R is a cycloalkylalkyl group. "[Cycloalkylalkyl][alkyl]amine" means
—N(R)$_2$ wherein one R is cycloalkylalkyl and the other R is alkyl.

"Hetero" refers to the replacement of at least one carbon atom member in a ring system with at least one heteroatom selected from N, S, and O. "Hetero" also refers to the replacement of at least one carbon atom member in an acyclic system. A hetero ring system or a hetero acyclic system may have 1, 2, 3, 4 or 5 carbon atoms members replaced by a heteroatom.

"Heterocycloalkyl" means a cyclic 4- to 12-membered saturated aliphatic ring containing 1, 2, 3, 4 or 5 heteroatoms independently selected from N, O or S. When one heteroatom is S, it can be optionally mono- or di-oxygenated (i.e. —S(O)— or —S(O)$_2$—). When one heteroatom is N, it can be optionally substituted with alkyl, cycloalkyl, alkylene-cycloalkyl, heterocycloalkyl, alkylene-heterocycloalkyl, aryl, alkylene-aryl, heteroaryl, alkylene-heteroaryl, each of which can be optionally substituted with one or more halogen, =O, hydroxy, alkoxy, haloalkyl, alkyl, etc.

A heterocycloalkyl moiety can be monocyclic, fused bicyclic, bridged bicyclic, spiro bicyclic, or polycyclic. For example, monocyclic (C$_3$-C$_8$) heterocycloalkyl means a 3- to 8 membered saturated aliphatic ring containing 1, 2, 3, 4, or 5 heteroatoms independently selected from N, O or S arranged in a monocyclic ring. Examples of monocyclic heterocycloalkyls include, but are not limited to, azetidine, pyrrolidine, piperidine, piperazine, azepane, hexahydropyrimidine, tetrahydrofuran, tetrahydropyran, morpholine, thiomorpholine, thiomorpholine 1,1-dioxide, tetrahydro-2H-1,2-thiazine, tetrahydro-2l1H-1,2-thiazine 1,1-dioxide, isothiazolidine, isothiazolidine 1,1-dioxide.

"Halogen," as used herein, refers to fluorine, chlorine, bromine, or iodine.

Haloalkyl and halocycloalkyl include mono, poly, and perhalo-substituted alkyl or cycloalkyl groups where each halogen is independently selected from fluorine, chlorine, and bromine.

"Haloalkoxy" means an alkyl radical attached through an oxygen linking atom where the alkyl chain is substituted with one or more halogen.

"Halogen" and "halo" are interchangeably used herein and each refers to fluorine, chlorine, bromine, or iodine.

"Fluoro" means —F.

As used herein, fluoro-substituted-$(C_1-C_4)$alkyl means a $(C_1-C_4)$alkyl substituted with one or more —F groups. Examples of fluoro-substituted-$(C_1-C_4)$alkyl include, but are not limited to, —$CF_3$, —$CH_2CF_3$, —$CH_2CF_2H$, —$CH_2CH_2F$ and —$CH_2CH_2CF_3$.

"Naturally occurring amino acid side chain moiety" refers to any amino acid side chain moiety present in a natural amino acid.

By "bromodomain" is meant a portion of a polypeptide that recognizes acetylated lysine residues. In one embodiment, a bromodomain of a BET family member polypeptide comprises approximately 110 amino acids and shares a conserved fold comprising a left-handed bundle of four alpha helices linked by diverse loop regions that interact with chromatin.

By "BET family polypeptide" is meant a polypeptide comprising two bromodomains and an extraterminal (ET) domain or a fragment thereof having transcriptional regulatory activity or acetylated lysine binding activity. Exemplary BET family members include BRD2, BRD3, BRD4 and BRDT.

The term "pharmaceutically acceptable salt" also refers to a salt prepared from a compound disclosed herein, or any other compound delineated herein (e.g., a compound of Formulas I-III), having a basic functional group, such as an amino functional group, and a pharmaceutically acceptable inorganic or organic acid. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

The term "pharmaceutically acceptable salt" also refers to a salt prepared from a compound disclosed herein (e.g., a compound of Formulas I-III) or any other compound delineated herein, having an acidic functional group, such as a carboxylic acid functional group, and a pharmaceutically acceptable inorganic or organic base.

Salts of the compounds used in the methods of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, quinine, quinoline, and basic amino acids such as lysine and arginine.

The invention also includes various isomers of the compounds disclosed herein and mixtures thereof. Certain compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomers" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity (i.e., they do not rotate the plane of polarized light).

The compounds of the present invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer that is present divided by the combined weight of the enantiomer that is present and the weight of its optical isomer.

As used herein, the term "tautomers" refers to isomers of organic molecules that readily interconvert by tautomerization, in which a hydrogen atom or proton migrates in the reaction, accompanied in some occasions by a switch of a single bond and an adjacent double bond.

Values and Alternative Values for Variables

The present invention is compounds represented by Formulas (I-III) or a pharmaceutically acceptable salt thereof. Values and alternative values for the variables in Formulas (I-III) or an enantiomer, a diastereomer, or a pharmaceutically acceptable salt thereof, and for each of the embodiments described herein are provided in the following paragraphs. It is understood that the invention encompasses all combinations of the substituent variables (i.e., $R_1$, $R_2$, $R_{20}$, etc.) defined herein.

A is selected from the group consisting of a $(C_1\text{-}C_6)$alkyl, a $(C_2\text{-}C_6)$alkenyl, a $(C_2\text{-}C_6)$alkynyl, a $(C_3\text{-}C_{12})$cycloalkyl, and a $(C_5\text{-}C_7)$heterocycloalkyl, wherein moiety A is optionally substituted with 1 to 4 $R_2$ groups.

Alternatively, A is selected from the group consisting of a $(C_1\text{-}C_6)$alkyl, a $(C_3\text{-}C_{12})$cycloalkyl, and a $(C_5\text{-}C_7)$heterocycloalkyl, wherein moiety A is optionally substituted with 1 to 4 $R_2$ groups. In another alternative, A is selected from the group consisting of a $(C_1\text{-}C_6)$alkyl, a $(C_3\text{-}C_{12})$cycloalkyl, and a $(C_5\text{-}C_7)$heterocycloalkyl. Further, A is ethyl or cyclohexyl.

$R_1$ is selected from the group consisting of —OH, a halogen, —CN, a $(C_1\text{-}C_4)$ alkoxy, —C(O)$(C_1\text{-}C_4)$alkyl, —C(O)O$(C_1\text{-}C_4)$alkyl, —OC(O)$(C_1\text{-}C_4$ alkyl), —C(O)NR$_3$R$_4$, —NR$_5$C(=O)R$_6$, a $(C_1\text{-}C_6)$alkyl, a $(C_2\text{-}C_6)$alkenyl, a $(C_3\text{-}C_{12})$cycloalkyl, and a $(C_5\text{-}C_7)$heterocycloalkyl.

Alternatively, $R_1$ is selected from the group consisting of —OH, a halogen, a $(C_1\text{-}C_4)$ alkoxy, —C(O)$(C_1\text{-}C_4)$alkyl, —C(O)O$(C_1\text{-}C_4)$alkyl, —OC(O)$(C_1\text{-}C_4$ alkyl) and a $(C_1\text{-}C_6)$ alkyl. Further, $R_1$ is selected from the group consisting of —OH, a halogen, $(C_1\text{-}C_4)$ alkoxy, and a $(C_1\text{-}C_6)$alkyl. Alternatively, $R_1$ is selected from the group consisting of a halogen and a $(C_1\text{-}C_6)$alkyl. In another alternative, $R_1$ is selected from the group consisting of —F, —Cl, —Br, or —I.

$R_2$ is a $(C_1\text{—}C)$alkyl, a $(C_2\text{-}C_6)$alkenyl, a halo$(C_1\text{-}C_6)$ alkoxy, a halo$(C_1\text{-}C_6)$alkyl, a hydroxy$(C_1\text{-}C_6)$alkyl, a $(C_1\text{-}C_6)$alkoxy$(C_1\text{-}C_6)$alkyl, a $(C_3\text{-}C_{12})$ cycloalkyl, a —$(C_1\text{-}C_6)$alkylene-$(C_3\text{-}C_{12})$cycloalkyl, a $(C_3\text{-}C_{12})$ heterocycloalkyl, a —$(C_1\text{-}C_6)$alkylene-$(C_3\text{-}C_{12})$heterocycloalkyl, a $(C_1\text{-}C_6)$ alkoxy, —C(O)$(C_1\text{-}C_6$ alkyl), —C(O)O$(C_1\text{-}C_6$ alkyl), —OC(O)$(C_1\text{-}C_6$ alkyl), —C(O)NR$_7$R$_8$, —NR$_9$C(=O)R$_{10}$, —NR$_{11}$R$_{12}$, a halogen, an oxo, or —OH.

Alternatively, $R_2$ is a $(C_1\text{-}C_6)$alkyl, a halo$(C_1\text{-}C_6)$alkoxy, a halo$(C_1\text{-}C_6)$alkyl, a hydroxy$(C_1\text{-}C_6)$alkyl, a $(C_1\text{-}C_6)$alkoxy $(C_1\text{-}C_6)$alkyl, a $(C_1\text{-}C_6)$alkoxy, —C(O)$(C_1\text{-}C_6$ alkyl), —C(O)O$(C_1\text{-}C_6$ alkyl), —OC(O)$(C_1\text{-}C_6$ alkyl), a halogen, an oxo, or —OH. Further, $R_2$ is a $(C_1\text{-}C_6)$alkyl, a halo$(C_1\text{-}C_6)$alkoxy, a halo$(C_1\text{-}C_6)$alkyl, a hydroxy$(C_1\text{-}C_6)$alkyl, a $(C_1\text{-}C_6)$alkoxy$(C_1\text{-}C_6)$alkyl, a $(C_1\text{-}C_6)$alkoxy, a halogen, an oxo, or —OH.

$R_3$ is H or a $(C_1\text{-}C_4)$alkyl. Alternatively, $R_3$ is H, methyl, ethyl, propyl, iso-propyl, butyl, iso-butyl, or tert-butyl.

$R_4$ is H or a $(C_1\text{-}C_4)$alkyl. Alternatively, $R_4$ is H, methyl, ethyl, propyl, iso-propyl, butyl, iso-butyl, or tert-butyl.

$R_5$ is H or a $(C_1\text{-}C_4)$alkyl. Alternatively, $R_5$ is H, methyl, ethyl, propyl, iso-propyl, butyl, iso-butyl, or tert-butyl.

$R_6$ is H or a $(C_1\text{-}C_4)$alkyl. Alternatively, $R_6$ is H, methyl, ethyl, propyl, iso-propyl, butyl, iso-butyl, or tert-butyl.

$R_7$ is 1H or a $(C_1\text{-}C_4)$alkyl. Alternatively, $R_7$ is H, methyl, ethyl, propyl, iso-propyl, butyl, iso-butyl, or tert-butyl.

$R_8$ is II or a $(C_1\text{-}C_4)$alkyl. Alternatively, $R_8$ is H, methyl, ethyl, propyl, iso-propyl, butyl, iso-butyl, or tert-butyl.

$R_9$ is H or a $(C_1\text{-}C_4)$alkyl. Alternatively, $R_9$ is H, methyl, ethyl, propyl, iso-propyl, butyl, iso-butyl, or tert-butyl.

$R_{10}$ is H or a $(C_1\text{-}C_4)$alkyl. Alternatively, $R_{10}$ is H, methyl, ethyl, propyl, iso-propyl, butyl, iso-butyl, or tert-butyl.

$R_{11}$ is H or a $(C_1\text{-}C_4)$alkyl. Alternatively, $R_{11}$ is H, methyl, ethyl, propyl, iso-propyl, butyl, iso-butyl, or tert-butyl.

$R_{12}$ is H or a $(C_1\text{-}C_4)$alkyl. Alternatively, $R_{12}$ is H, methyl, ethyl, propyl, iso-propyl, butyl, iso-butyl, or tert-butyl.

$R_{20}$ is —H, —OH, a $(C_1\text{-}C_3)$ alkyl, a $(C_3\text{-}C_{12})$cycloalkyl, or a $(C_5\text{-}C_7)$heterocycloalkyl. Alternatively, $R_{20}$ is H or a $(C_1\text{-}C_3)$alkyl. Further, $R_{20}$ is H, methyl, ethyl, propyl, or iso-propyl.

$R_{30}$ is —H, —OH, a $(C_1\text{-}C_3)$alkyl, a $(C_3\text{-}C_{12})$cycloalkyl, or a $(C_5\text{-}C_7)$heterocycloalkyl. Alternatively, $R_{30}$ is H or a $(C_1\text{-}C_3)$alkyl. Further, $R_{30}$ is H, methyl, ethyl, propyl, or iso-propyl.

$R_{40}$, for each occurence independently, is —H, —OH, a $(C_1\text{-}C_3)$alkyl, a $(C_3\text{-}C_{12})$cycloalkyl, or a $(C_5\text{-}C_7)$heterocycloalkyl. $R_{40}$ is H or a $(C_1\text{-}C_3)$alkyl. Further, $R_{40}$ is H, methyl, ethyl, propyl, or iso-propyl.

m is 0, 1, 2, 3, or 4. Alternatively, m is 0, 1, or 2. Further, m is 1 or 2. Alternatively, m is 1.

n is 0, 1, 2, 3, or 4. Alternatively, n is 0, 1, or 2. Further, n is 0 or 1. Alternatively, n is 1.

p is 0, 1, 2, 3 or 4. Alternatively, p is 0, 1, or 2. Further, p is 0 or 1.

q is 0, 1, 2, 3 or 4. Alternatively, q is 0, 1, or 2. Further, q is 0 or 1.

A description of example embodiments of the invention follows.

A first embodiment of the present invention is directed to a compound of Structural Formula I:

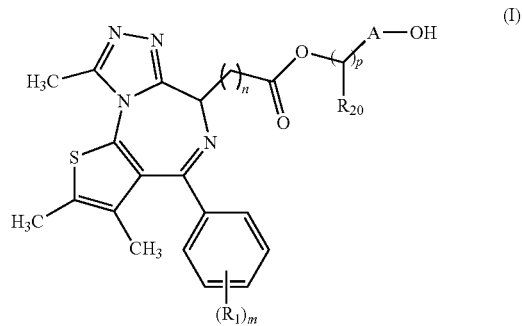

(I)

or a pharmaceutically acceptable salt thereof, wherein:

A is selected from the group consisting of a $(C_1\text{-}C_6)$alkyl, a $(C_2\text{-}C_6)$alkenyl, a $(C_2\text{-}C_6)$alkynyl, a $(C_3\text{-}C_{12})$cycloalkyl, and a $(C_5\text{-}C_7)$heterocycloalkyl, wherein moiety A is optionally substituted with 1 to 4 $R_2$ groups;

$R_{20}$, for each occurence independently, is —H, —OH, a $(C_1\text{-}C_3)$ alkyl, a $(C_3\text{-}C_{12})$cycloalkyl, or a $(C_5\text{-}C_7)$heterocycloalkyl;

$R_1$ for each occurence independently is selected from the group consisting of —OH, a halogen, —CN, a $(C_1\text{-}C_4)$ alkoxy, —C(O)$(C_1\text{-}C_4)$alkyl, —C(O)O$(C_1\text{-}C_4)$alkyl, —OC(O)$(C_1\text{-}C_4$ alkyl), —C(O)NR$_3$R$_4$, —NR$_5$C(=O)R$_6$, a $(C_1\text{-}C_6)$alkyl, a $(C_2\text{-}C_6)$alkenyl, a $(C_3\text{-}C_{12})$cycloalkyl, and a $(C_5\text{-}C_7)$heterocycloalkyl;

$R_2$ for each occurence independently is a $(C_1\text{-}C_6)$alkyl, a $(C_2\text{-}C_6)$alkenyl, a halo$(C_1\text{-}C_6)$alkoxy, a halo$(C_1\text{-}C_6)$alkyl, a hydroxy$(C_1\text{-}C_6)$alkyl, a $(C_1\text{-}C_6)$alkoxy$(C_1\text{-}C_6)$alkyl, a $(C_3\text{-}C_{12})$ cycloalkyl, a —$(C_1\text{-}C_6)$alkylene-$(C_3\text{-}C_{12})$cycloalkyl, a $(C_3\text{-}C_{12})$ heterocycloalkyl, a —$(C_1\text{-}C_6)$alkylene-$(C_3\text{-}C_{12})$ heterocycloalkyl, a $(C_1\text{-}C_6)$alkoxy, —C(O)$(C_1\text{-}C_6$ alkyl), —C(O)O$(C_1\text{-}C_6$ alkyl), —OC(O)$(C_1\text{-}C_6$ alkyl), —C(O)NR$_7$R$_8$, —NR$_9$C(=O)R$_{10}$, —NR$_{11}$R$_{12}$, a halogen, an oxo, or —OH;

$R_3$, $R_4$, $R_5$, $R_6$, $R_7$, $R_8$, $R_9$, $R_{10}$, $R_{11}$, and $R_{12}$ are each independently H or a $(C_1\text{-}C_4)$alkyl; and each m, n and p is independently 0, 1, 2, 3, or 4.

In a first aspect of the first embodiment: A is a $(C_1-C_6)$ alkyl, a $(C_3-C_{12})$cycloalkyl, or a $(C_5-C_7)$heterocycloalkyl.

In a second aspect of the first embodiment: A is ethyl or cyclohexyl.

In a third aspect of the first embodiment: $R_2$ is —OH or a $(C_1-C_6)$alkyl. In a particular example of the third aspect, the remaining variables are as set forth in the first or second aspect of the first embodiment.

In a fourth aspect of the first embodiment: $R_2$ is —OH or methyl. In a particular example of the third aspect, the remaining variables are as set forth in the first or second aspect of the first embodiment.

In a fifth aspect of the first embodiment: $R_1$ is —F, —Cl, —Br, or —I. In a particular example of the fifth aspect, the remaining variables are as in the first, second, third or fourth aspect of the first embodiment or any of the particular examples of the third or fourth aspect.

In a sixth aspect of the first embodiment: $R_{20}$ is H or a $(C_1-C_3)$alkyl. In a particular example of the sixth aspect, the remaining variables are as in the first, second, third, fourth or fifth aspect of the first embodiment or any of the particular examples of the third, fourth or fifth aspect.

In a seventh aspect of the first embodiment: p is 0. In a particular example of the seventh aspect, the remaining variables are as in the first, second, third, fourth, fifth or sixth aspect of the first embodiment or any of the particular examples of the third, fourth or fifth or sixth aspect.

In an eighth aspect of the first embodiment: m is 1. In a particular example of the eighth aspect, the remaining variables are as in the first, second, third, fourth, fifth, sixth or seventh aspect of the first embodiment or any of the particular examples of the third, fourth, fifth, sixth or seventh aspect.

In a ninth aspect of the first embodiment: n is 1. In a particular example of the ninth aspect, the remaining variables are as in the first, second, third, fourth, fifth, sixth, seventh or eighth aspect of the first embodiment or any of the particular examples of the third, fourth, fifth, sixth, seventh or eighth aspect.

In a second embodiment, the present invention is directed to a compound of Structural Formula II:

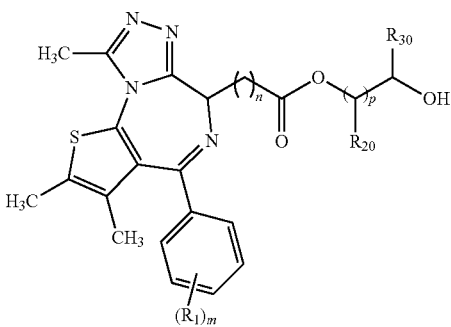

(II)

or a pharmaceutically acceptable salt thereof, wherein:

$R_1$ for each occurence independently is selected from the group consisting of —OH, a halogen, —CN, a $(C_1-C_4)$ alkoxy, —C(O)$(C_1-C_4)$alkyl, —C(O)O$(C_1-C_4)$alkyl, —OC(O)$(C_1-C_4$ alkyl), —C(O)NR$_3$R$_4$, —NR$_5$C(=O)R$_6$, a $(C_1-C_6)$alkyl, a $(C_2-C_6)$alkenyl, a $(C_3-C_{12})$cycloalkyl, and a $(C_5-C_7)$heterocycloalkyl;

$R_3$, $R_4$, $R_5$, and $R_6$ are each independently H or a $(C_1-C_4)$alkyl $R_{20}$, for each occurence independently, is —H, —OH, a $(C_1-C_3)$ alkyl, a $(C_3-C_{12})$cycloalkyl, or a $(C_5-C_7)$heterocycloalkyl;

$R_{30}$, for each occurence independently, is —H, —OH, a $(C_1-C_3)$alkyl, a $(C_3-C_{12})$cycloalkyl, or a $(C_5-C_7)$heterocycloalkyl; and each m, n and p is independently 0, 1, 2, 3, or 4.

In a first aspect of the second embodiment: $R_1$ is —F, —Cl, —Br, or I.

In a second aspect of second embodiment: $R_{20}$ is H or a $(C_1-C_3)$alkyl. In a particular example of the second aspect, the remaining variables are as set forth in the first aspect of the second embodiment.

In a third aspect of the second embodiment: $R_{30}$ is H or a $(C_1-C_3)$alkyl. In a particular example of the third aspect, the remaining variables are as set forth in the first or second aspect of the second embodiment or any of the particular examples of the second aspect.

In a fourth aspect of the second embodiment: p is 1. In a particular example of the fourth aspect, the remaining variables are as set forth in the first, second or third aspect of the second embodiment or any of the particular examples of the second or third aspect.

In a fifth aspect of the second embodiment: m is 1. In a particular example of the fifth aspect, the remaining variables are as set forth in the first, second, third or fourth aspect of the second embodiment or any of the particular examples of the second, third or fourth aspect.

In a sixth aspect of the second embodiment: n is 1. In a particular example of the sixth aspect, the remaining variables are as set forth in the first, second, third, fourth or fifth aspect of the second embodiment or any of the particular examples of the second, third, fourth or fifth aspect.

In a third embodiment, the present invention is directed to a compound of Structural Formula III:

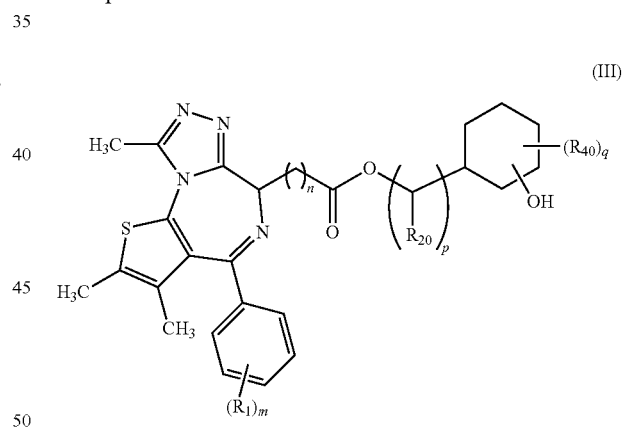

(III)

or a pharmaceutically acceptable salt thereof, wherein:

$R_1$ for each occurence independently is selected from the group consisting of —OH, a halogen, —CN, a $(C_1-C_4)$ alkoxy, —C(O)$(C_1-C_4)$alkyl, —C(O)O$(C_1-C_4)$alkyl, —OC(O)$(C_1-C_4$ alkyl), —C(O)NR$_3$R$_4$, —NR$_5$C(=O)R$_6$, a $(C_1-C_6)$alkyl, a $(C_2-C_6)$alkenyl, a $(C_3-C_{12})$cycloalkyl, and a $(C_5-C_7)$heterocycloalkyl;

$R_3$, $R_4$, $R_5$, and $R_6$ are each independently H or a $(C_1-C_4)$alkyl $R_{20}$, for each occurence independently, is —H, —OH, a $(C_1-C_3)$ alkyl, a $(C_3-C_{12})$cycloalkyl, or a $(C_5-C_7)$heterocycloalkyl;

$R_{40}$, for each occurence independently, is —H, —OH, a $(C_1-C_3)$alkyl, a $(C_3-C_{12})$cycloalkyl, or a $(C_5-C_7)$heterocycloalkyl; and (00117) each q, m, n and p is independently 0, 1, 2, 3 or 4.

In one aspect of the third embodiment: $R_1$ is —F, —Cl, —Br, or —I.

In a second aspect of third embodiment: $R_{20}$ is H or a ($C_1$-$C_3$)alkyl. In a particular example of the second aspect, the remaining variables are as set forth in the first aspect of the third embodiment.

In a third aspect of the third embodiment: $R_{40}$ is H or a ($C_1$-$C_3$)alkyl. In a particular example of the third aspect, the remaining variables are as set forth in the first or second aspect of the third embodiment or any of the particular examples of the second aspect.

In a fourth aspect of the third embodiment: p is 0. In a particular example of the fourth aspect, the remaining variables are as set forth in the first, second or third aspect of the third embodiment or any of the particular examples of the second or third aspect.

In a fifth aspect of the third embodiment: m is 1. In a particular example of the fifth aspect, the remaining variables are as set forth in the first, second, third or fourth aspect of the third embodiment or any of the particular examples of the second, third or fourth aspect.

In a sixth aspect of the third embodiment: n is 1. In a particular example of the sixth aspect, the remaining variables are as set forth in the first, second, third, fourth or fifth aspect of the third embodiment or any of the particular examples of the second, third, fourth or fifth aspect.

In another aspect, the invention provides a compound represented by any one of the following formulae:

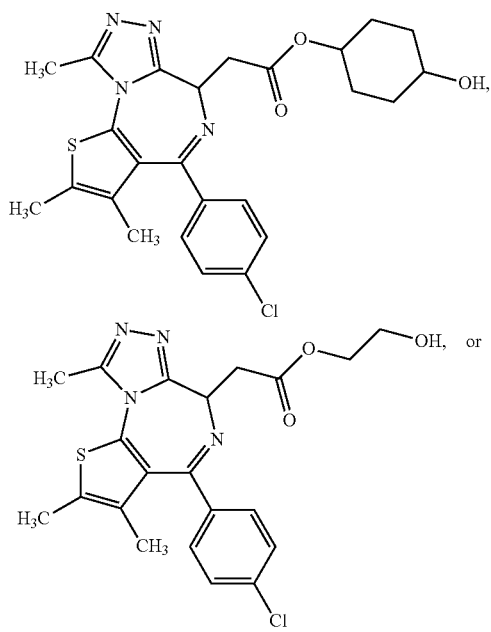

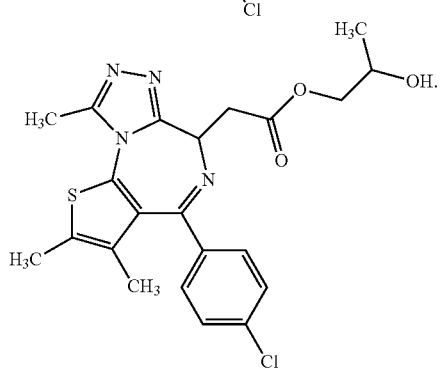

or a pharmaceutically acceptable salt thereof.

In another aspect, the invention provides a compound represented by any one of the following formulae:

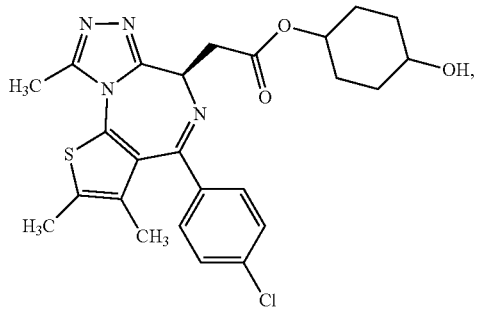

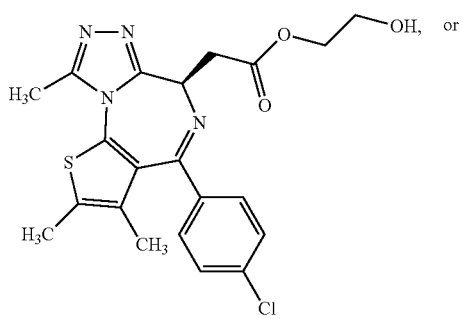

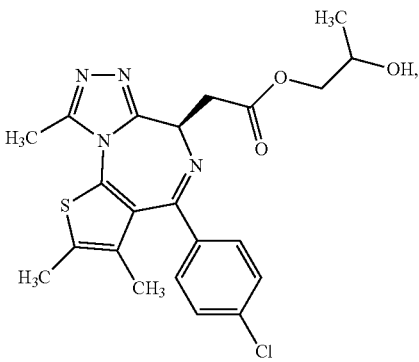

or a pharmaceutically acceptable salt thereof.

In another aspect, the invention provides a compound represented by any one of the following formulae:

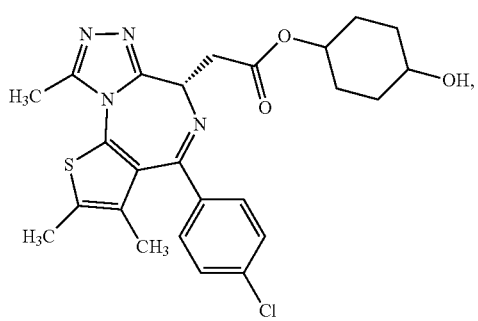

15
-continued
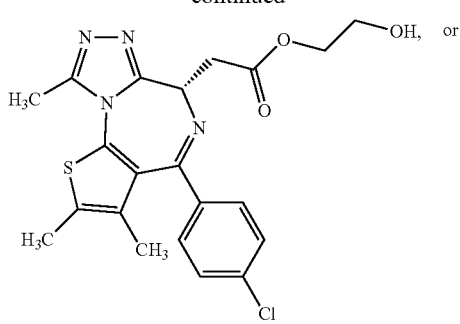
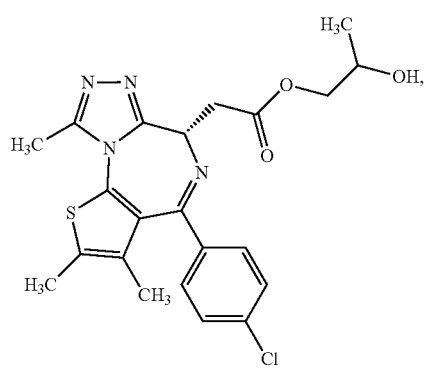
or a pharmaceutically acceptable salt thereof.
In another aspect, the invention provides a compound represented by any one of the following formulae:
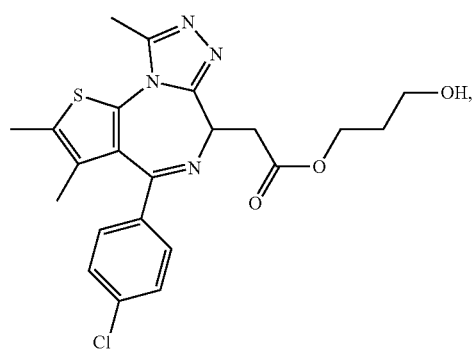
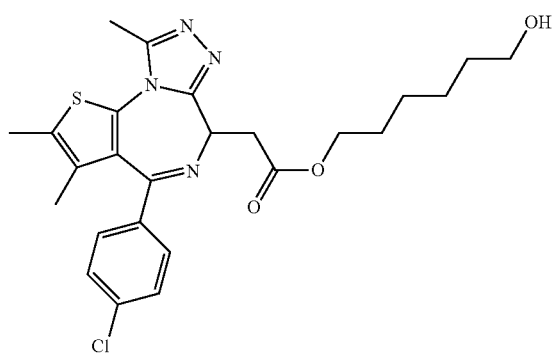
16
-continued
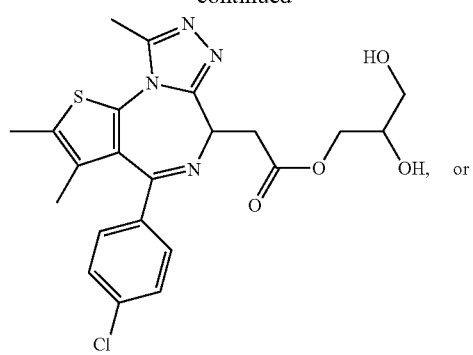
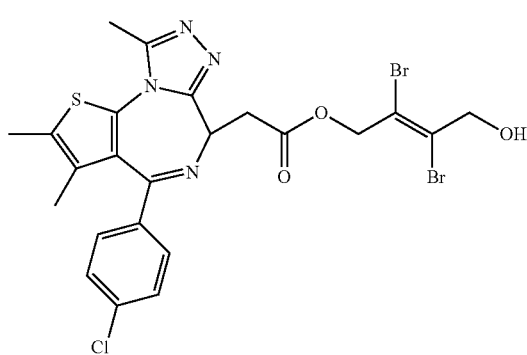
or a pharmaceutically acceptable salt thereof.
In another aspect, the invention provides a compound represented by any one of the following formulae:
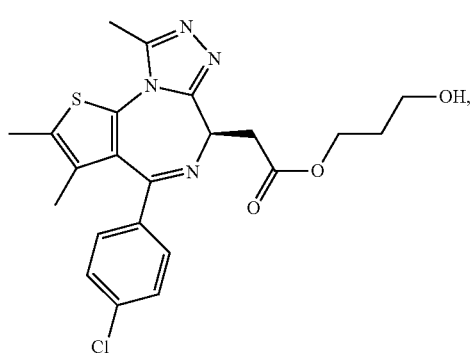
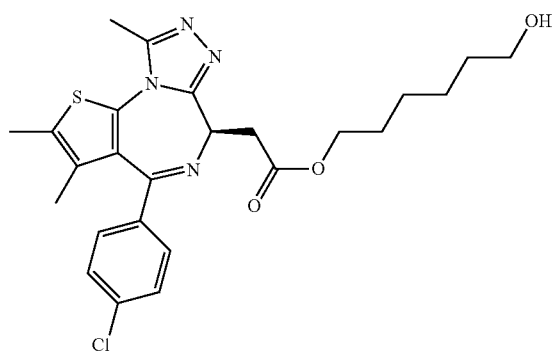

-continued

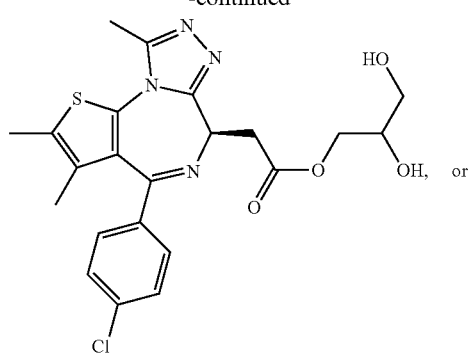

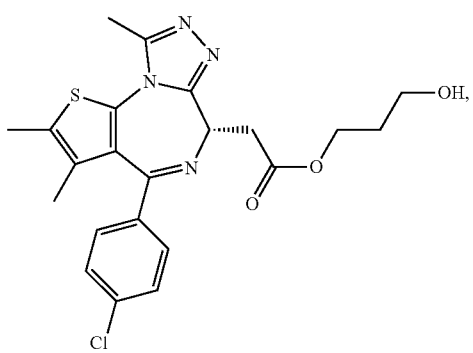

or a pharmaceutically acceptable salt thereof.

In another aspect, the invention provides a compound represented by any one of the following formulae:

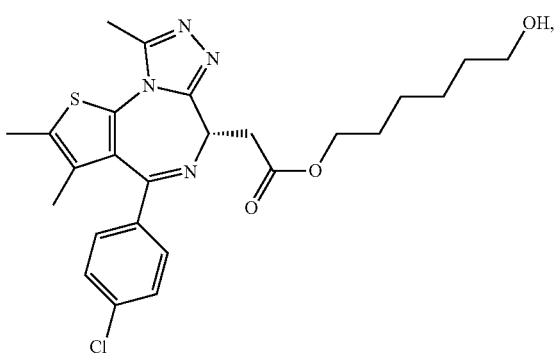

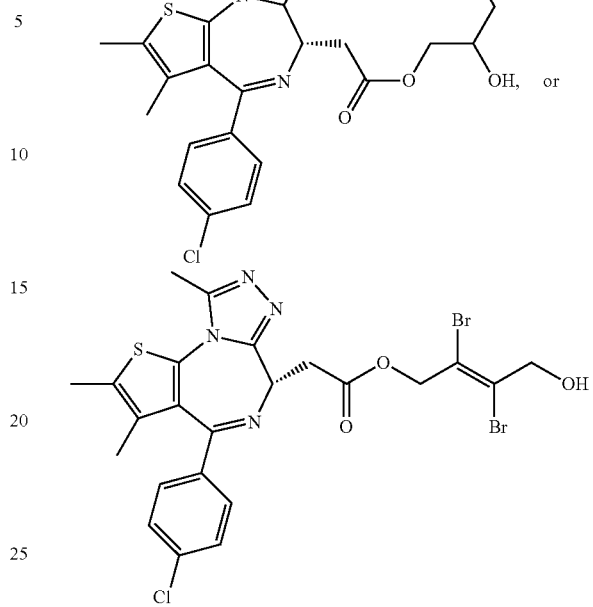

or a pharmaceutically acceptable salt thereof.

In fourth embodiment, the present invention is directed to a method of treating a disorder responsive to the modulation of a BET family polypeptide in a subject in need thereof, comprising administering to the subject an effective amount of a compound represented by Structural Formula (I), (II) or (III) or any of the aspects or particular examples or specific compounds described herein.

In a first aspect of the fourth embodiment, the BET family member is BRD2, BRD3, BRD4 or BRDT.

In another aspect, the invention provides a packaged pharmaceutical comprising a therapeutically effective amount of any compound described herein, and written instructions for administration of the compound for any one of the diseases or disorders described herein.

By "BET family polypeptide" is meant a polypeptide comprising two bromodomains and an extraterminal (ET) domain or a fragment thereof having transcriptional regulatory activity or acetylated lysine binding activity. Exemplary BET family members include BRD2, BRD3, BRD4 and BRDT.

In a second aspect of the fourth embodiment, the modulation of a BET family polypeptide comprises binding to a bromodomain of a BET polypeptide.

In a third aspect of the fourth embodiment, the modulation of a BET family polypeptide comprises binding to a BET family bromodomain and disrupting bromodomain interaction with chromatin, thereby treating the disorder.

In a fifth embodiment, the present invention is a pharmaceutical composition comprising one or more pharmaceutically acceptable carriers and/or diluents and an effective amount of a compound disclosed herein (e.g., an effective amount of a compound represented by Structural Formula (I), (II) or (III) or any of the aspects or particular examples thereof or specific compounds described herein).

In a sixth embodiment, the present invention is a method of treating a disorder responsive to the modulation of a BET family polypeptide in a subject in need thereof, comprising administering to the subject an effective amount of a pharmaceutical composition comprising one or more pharmaceutically acceptable carriers and/or diluents and a compound represented by Structural Formula (I), (II) or (III) or any of the aspects or particular examples or specific compounds described herein. In another embodiment, the BET family member is BRD2, BRD3, BRD4 or BRDT.

In a seventh embodiment, the present invention is a method of treating a disorder responsive to the modulation of a BET family polypeptide in a subject in need thereof, the method comprising administering an effective amount of a compound represented by Structural Formula (I), (II) or (III) or any of the aspects or particular examples or specific compounds described herein or a pharmaceutically acceptable salt thereof. In one aspect, said compound is capable of binding a BET family bromodomain and disrupting bromodomain interaction with chromatin, thereby treating the disorder. In another aspect, said compound is capable of binding a BET family bromodomain and inhibiting bromodomain binding to chromatin in a cellular environment.

Disease" and "disorder" are used interchangeably and mean any condition that damages or interferes with the normal function of a cell, tissue, or organ.

Disorders responsive to the modulation of a BET family polypeptide include those described below.

The present invention features methods for treating or preventing a neoplasia, an inflammatory disease, metabolic syndrome, obesity, fatty liver (NASH or otherwise), diabetes (e.g., type II diabetes), atherosclerosis, arterial stent occlusion, heart failure, conditions associated with hyperinsulinaemia, cachexia, graft versus host disease, infection diseases associated with bromodomains, the treatment of parasites, malaria, trypanosomes, and for reducing male fertility. Further uses of the compositions of the invention include, but are not limited to, use in organ transplantation, modulation of cell state for regenerative medicine (i.e., by promoting or inhibiting cellular differentiation), and facilitating pluripotency.

In certain embodiments, the subject is a mammal. In certain embodiments, the subject is a human patient.

In certain embodiments, the method reduces the growth or proliferation of a neoplasia in a subject.

In certain embodiments, the BET family member is BRD2, BRD3, BRD4 or BRDT.

In certain embodiments, the neoplasia is driven by a transcriptional activator. In certain embodiments, the transcriptional activator is myc.

In certain embodiments, the subject has a neoplasia selected from the group consisting of hematological neoplasia (e.g., lymphoma, myeloma, leukemia), lung cancer, breast cancer, colon cancer, prostate cancer, cervical cancer, neuroblastoma, glial blastoma multiforme, medulloblastoma, malignant peripheral nerve sheath tumor, melanoma, NUT midline carcinoma, squamous cell carcinoma or any other carcinoma associated with a NUT rearrangement.

In one aspect, the invention provides a method for treating a hematological cancer selected from leukemia, lymphoma or myeloma. Specific examples include, but are not limited to, acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Burkitt's lymphoma, MLL driven leukemia chronic lymphocytic leukemia, Eosinophilic Leukemia, Hairy Cell Leukemia, Hodgkin Lymphoma, Multiple Myeloma, Non-Hodgkin Lymphoma, Myeloproliferative disorders or Myelodysplastic syndromes).

The term "neoplastic" refers to those cells having the capacity for autonomous growth, i.e., an abnormal state or condition characterized by rapidly proliferating cell growth. A neoplastic disease state may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the term neoplasia generally refers to cells experiencing abnormal cell growth rates. Neoplasias include "tumors," which may be either benign, premalignant or malignant.

As described herein, the present invention features methods for treating and/or preventing metabolic syndrome, obesity, fatty liver (NASH or otherwise), diabetes (e.g., type II diabetes), insulin resistance, atherosclerosis, arterial stent occlusion, heart failure and related disorders characterized by undesirable alterations in metabolism or fat accumulation.

In one aspect, the invention provides a method of inhibiting adipogenesis, the method involving contacting an adipocyte or pre-adipocyte with an effective amount of a compound described herein.

In another aspect, the invention provides a method of inhibiting adipocyte biological function, the method involving contacting an adipocyte with an effective amount of a compound described herein.

In yet another aspect, the invention provides a method for treating or preventing metabolic syndrome in a human, the method involving administering to the human an effective amount of a compound described herein.

In further aspects, the invention provides a method for treating or preventing obesity or weight gain in a human, the method involving administering to the human an effective amount of a compound described herein.

In another aspect, the invention provides a method of inhibiting hepatic steatosis in a human, the method involving administering to the human an effective amount of a compound described herein.

In a further aspect, the invention provides a method of reducing subcutaneous fat or visceral fat in a human, the method involving administering to the human an effective amount of a compound described herein.

In yet another aspect, the invention provides a method of inhibiting food intake or increasing metabolism in a human, the method involving administering to the human an effective amount of a compound described herein.

In an additional aspect, the invention provides a kit for the treatment of a body weight disorder, the kit comprising an effective amount of a compound described herein and directions for use of the kit to practice any of the methods disclosed herein.

In various embodiments of the above aspects or any other aspect of the invention delineated herein, the method inhibits adipocyte differentiation, proliferation, or hypertrophy. In another embodiment the method reduces fatty acid synthesis, lipogenesis, lipid droplet accumulation. In further embodiments the method reduces abdominal obesity, atherogenic dyslipidemia, elevated blood pressure, insulin resistance, or type II diabetes.

By "adipogenesis" is meant an increase in the number of adipocytes. Adipogenesis typically involves hyperplasia (increase in number) of adipocytes. Adipocyte hypertrophy is the increase in size of a pre-existing adipocyte as a result of excess triglyceride accumulation. Hypertrophy occurs when energy intake exceeds energy expenditure. Hyperplasia results from the formation of new adipocytes from precursor cells in adipose tissue. Typically hyperplasia involves the proliferation of preadipocytes and their differentiation into adipocytes.

By "body weight disorder" is meant any disorder or disease that results in an abnormal body weight.

By "metabolic syndrome" is meant one or more risk factors that increase a subject's propensity to develop coronary heart disease, stroke, peripheral vascular disease and/or type II diabetes. Risk factors associated with metabolic syndrome include abdominal obesity (i.e, excessive fat tissue in and around the abdomen, atherogenic dyslipidemia including but not limited to high triglycerides, low HDL cholesterol and high LDL cholesterol, elevated blood pressure, insulin resistance or glucose intolerance, Prothrombotic state (e.g., high fibrinogen or plasminogen activator inhibitor-1 in the blood), proinflammatory state (e.g., elevated C-reactive protein in the blood). Agents of the invention are useful for the treatment or prevention of metabolic syndrome in a subject having one or more of the aforementioned risk factors.

By "obesity" is meant an excess of body fat relative to lean body mass. A subject is considered obese if they have a body mass index (BMI) of 30 and above.

By "body mass index (BMI)" is a subject's weight in kilograms divided by their height in meters squared.

By "weight gain" is meant an increase in body weight relative to the body weight of the individual at an earlier point in time or relative to a reference body weight. In one embodiment, a reference body weight corresponds to a BMI of about 25.

As described below, this invention provides methods for using compounds described herein to decrease male fertility. In one embodiment the compounds described herein can be used as a male contraceptive.

In one aspect, the invention provides methods for reducing or inhibiting spermatogenesis in a male subject. The methods involve administering an effective amount of a compound or a salt thereof described herein to the male subject.

In one aspect, the invention provides methods for reducing the rate of male fertility in a subject. In embodiments, the methods involve administering an effective amount of a compound or a salt thereof to the male subject.

In the above aspects, the methods involve administering the compound or a salt thereof in an amount sufficient to reduce sperm number and/or reduce sperm motility.

In the above aspects, the methods involve administering the compound or a salt thereof as described herein in an amount sufficient to induce azoospermia, oligozoospermia, and/or asthenozoospermia. In embodiments, the methods induce a contraceptive effect in the subject.

In embodiments, the compound or a salt thereof is present in an amount effective to reduce sperm number and/or reduce sperm motility.

In embodiments, the compound or a salt thereof is present in a amount effective to induce azoospermia, oligozoospermia, and/or asthenozoospermia. In related embodiments, the compound or a salt thereof is present in a amount effective to induce a contraceptive effect in the subject.

The term "reducing or inhibiting spermatozoa emission" refers to lowering the amount of spermatozoa present in seminal fluid during discharge of the seminal fluid from a male subject. Reduction or inhibition of spermatozoa levels in seminal fluid can be effected by suppressing spermatogenesis, inducing azoospermia, inducing oligozoospermia, and the like. Thus, in the context of the present invention, "reducing or inhibiting spermatozoa emission" has the effect of inhibiting and/or reducing the rate of fertilization when the discharged seminal fluid contacts ova from a female subject.

"Spermatogenesis" refers to the overall process of gametogenesis in the male. Spermatogenesis takes place in the seminiferous tubule and is directly regulated by levels of follicle stimulating hormone and androgen at the periphery of the seminiferous tubule, particularly upon the Sertoli cells.

The term "azoospermia" refers to a spermatozoa content below 1 million per mL seminal fluid, approaching levels of zero spermatozoa content, and are the result of suppression of spermatogenesis.

The term "oligozoospermia" refers to a spermatozoa content between 20 and one million per mL (mill/mL) seminal fluid, and are the result of inhibited levels of spermatogenesis.

Another embodiment of the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound described herein.

As used herein the term "subject" and "patient" typically means a human, but can also be an animal in need of treatment, e.g., companion animals (dogs, cats, and the like), farm animals (cows, pigs, horses, sheep, goats, and the like), and laboratory animals (rats, mice, guinea pigs, and the like).

The terms "treat" and "treating" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein, a disorder responsive to the modulation of a BET family polypeptide), lessen the severity of the disease or improve the symptoms associated with the disease delineated herein. As used herein, the term "effective amount" refers to an amount which, when administered in a proper dosing regimen, is sufficient to treat (therapeutically or prophylactically) the target disorder, in this case, a disorder responsive to the modulation of a BET family polypeptide. For example, an effective amount is sufficient to reduce or ameliorate the severity, duration, or progression of the disorder being treated, prevent the advancement of the disorder being treated, cause the regression of the disorder being treated, or enhance or improve the prophylactic or therapeutic effect(s) of another therapy. For example, an effective amount can be an amount or a combination thereof. An effective amount may contain from about 0.001 mg/kg/day to about 1000 mg/kg/day. In one embodiment, the effective amount of a compound of the invention is from about 0.001 mg/kg/day to about 100 mg/kg/day. In another embodiment, the effective amount of a compound of the invention is from about 0.01 mg/kg/day to about 50 mg/kg/day. In yet another embodiment, the effective amount of a compound of the invention is from about 0.01 mg/kg/day to about 25 mg/kg/ day. In yet another embodiment, the effective amount of a compound of the invention is from about 0.02 mg/kg/day to about 10 mg/kg/day. In yet another embodiment, the effective amount of a compound of the invention is from about 0.03 mg/kg/day to about 6 mg/kg/day, such as from about 0.03 mg/kg/day to about 3 mg/kg/day. In yet another embodiment, the effective amount of a compound of the invention is from about 0.1 mg/kg/day to about 10 mg/kg/day.

Modes of Administration

The compositions used in the present invention include ocular, oral, nasal, transdermal, topical with or without occlusion, intravenous (both bolus and infusion), inhalable, and injection (intraperitoneally, subcutaneously, intramuscularly, intratumorally, or parenterally) formulations. In a particular embodiment, the compositions are for intravenous or oral administration. The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

"Pharmaceutically acceptable carrier" and "pharmaceutically acceptable diluent" means non-therapeutic components that are of sufficient purity and quality for use in the formulation of a composition of the invention that, when appropriately administered to an animal or human, typically do not produce an adverse reaction, and that are used as a vehicle for a drug substance (i.e., a compound of the present invention). A description of specific carriers and combinations of carriers is provided below for each type of administration.

Compositions used in the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions used in the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains an effective amount of the active ingredient necessary to provide a therapeutic effect. The composition may contain from about 5,000 mg to about 0.01 mg of a compound of the invention, or pharmaceutically acceptable salt thereof, and may be constituted into any form suitable for the selected mode of administration. In one embodiment, the composition comprises about 5000 mg to about 0.01 mg of a compound of the invention, or pharmaceutically acceptable salt thereof. In another embodiment, the composition comprises about 1000 mg to about 0.01 mg of a compound of the invention, or pharmaceutically acceptable salt thereof. In yet another embodiment, the composition comprises about 100 mg to about 0.01 mg of a compound of the invention, or pharmaceutically acceptable salt thereof. The composition may be administered about 1 to about 5 times per day. Daily administration or periodic dosing may be employed.

For oral administration, the composition is preferably in the form of a tablet or capsule containing (e.g., 2000 to 0.5 milligrams of the active compound). Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or film-coated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate, or combinations thereof) may be used.

Compounds of the invention may also be administered via a slow release composition, wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles or nanoemulsions (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound disclosed herein and used in the methods of the invention may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired. In one embodiment, the compound, or a pharmaceutically acceptable salt thereof, is administered orally. In another embodiment, the compound, or a pharmaceutically acceptable salt thereof, is administered intravenously. The compounds of the present invention may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit can contain from about 0.005 to about 99% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

In another embodiment, the compounds of this invention may be administered directly to the lungs by inhalation.

Compounds of the invention may also be administered topically or enhanced by using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

Combination Therapy

In certain embodiments, the methods of the present invention also include treatment of a disorder responsive to the modulation of a BET family polypeptide using a compound of the invention, or a pharmaceutically acceptable salt thereof, alone or in combination with one or more therapeutic agents. The one or more therapeutic agents can be, for example, any agent that is capable of treating any of the disorders described herein that can be responsive to the modulation of a BET family polypeptide. Examples of therapeutic agents known in the art to treat a disorder responsive to the modulation of a BET family polypeptide and suitable for use in combination with the compounds of the invention include, but are not limited to daunorubicin, Ara-C, pomalidomide, lenalidomide, velcade, dexamethasone, rituximab, fulvestrant, ibrutinib and ponatinib.

Additionally, therapeutic agents known in the art to be an epigenetic or transcriptional modulator (e.g., DNA methyltransferase inhibitor, histone deacetylase inhibitor (HDAC inhibitor), lysine methyltransferase inhibitor) and suitable for use in combination with the compounds of the invention include. Such agents include panobinostat.

In another embodiment, the combination therapy comprises a compound of the invention, or a pharmaceutically acceptable salt thereof, and a therapeutic agent known in the art to treat a disorder responsive to the modulation of a BET family polypeptide, or a pharmaceutically acceptable salt thereof. In yet another embodiment, the combination therapy comprises a compound of the invention, or a pharmaceutically acceptable salt thereof, and a therapeutic agent known in the art to be an epigenetic or transcriptional modulator (e.g., DNA methyltransferase inhibitor, histone deacetylase inhibitor (HDAC inhibitor), lysine methyltransferase inhibitor), or a pharmaceutically acceptable salt thereof.

The language "in combination with" or "combination therapy" refers to the co-administration of a first amount of a compound capable of treating a disorder responsive to the modulation of a BET family polypeptide or a pharmaceutically acceptable salt thereof, and a second amount of at least one therapeutic agent, or a pharmaceutically acceptable salt thereof, wherein the first and second amounts together comprise a therapeutically effective amount to treat a disorder responsive to the modulation of a BET family polypeptide. Combination therapy encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of the compound capable of treating a disorder responsive to the modulation of a BET family polypeptide, or a pharmaceutically acceptable salt thereof, and a second amount of at least one therapeutic agent, or a pharmaceutically acceptable salt thereof, the compounds are administered sufficiently close in time to have the desired therapeutic effect. For example, the period of time between each administration, which can result in the desired therapeutic effect, can range from minutes to hours and can be determined taking into account the properties of each compound such as potency, solubility, bioavailability, plasma half-life and kinetic profile. For example, the compound capable of treating a disorder responsive to the modulation of a BET family polypeptide, or a pharmaceutically acceptable salt thereof, and at least one therapeutic agent, or a pharmaceutically acceptable salt thereof, can be administered in any order within about 24 hours of each other, within about 16 hours of each other, within about 8 hours of each other, within about 4 hours of each other, within about 1 hour of each other or within about 30 minutes of each other.

EXEMPLIFICATION

The following abbreviations are used in throughout the application.
Ac acetyl
AcOH acetic acid
AIBN 2,2'-azobis(2-methylpropionitrile)
aq aqueous
Asp aspartic acid
BET Bromodomain and extra-terminal domain
BRDT Bromodomain testis-specific protein
BRD2 Bromodomain containing protein 2
BRD3 Bromodomain containing protein 3
Brd4 Bromodomain containing protein 4
Bn benzyl
Boc tert-butoxycarbonyl
BOP (Benzotriazol-1-yloxy)tris(dimethylamino)phosphonium hexafluorophosphate
BSA bovine serum albumen
Bu butyl
DIPEA N,N-diisopropylethylamine
DMEM Dulbecco's Modified Eagle's medium
DMF N,N-dimethylformamide
DMSO dimethyl sulfoxide
EDC N-(3-dimethylaminopropyl)-N'-ethylcarbodiimide
ESI electrospray ionization
Et ethyl
EtOAc ethyl acetate
EtOH ethanol
Fmoc Fluorenylmethyloxycarbonyl
HCTU (2-(6-chloro-1H-benzotriazole-1-yl)-1,1,3,3-tetramethylaminium hexafluorophosphate
His histidine
HPLC high performance liquid chromatography
HRMS high resolution mass spectrometry
i iso
$IC_{50}$ Half maximal growth inhibitory concentration
i-$Pr_2$NEt N,N-Diisopropylethylamine
$K_2$EDTA Dipotassium ethylenediamine tetraacetate
KOt-Bu Potassium tert-butoxide
MBTE Methyl tert-butyl ether
MEG Monoethylene glycol
MeOH methanol
Me methyl
$MgSO_4$ Magnesium Sulfate
MS mass spectrometry
MW molecular weight
$Na_2$EDTA Disodium ethylenediamine tetraacetate
NMR nuclear magnetic resonance spectrometry
Papp Apparent permeability
PBS Phosphate buffered saline
Ph phenyl
PEG Polyethylene glycol
PO(OEt)$_2$Cl Diethyl chlorophosphate
Pr propyl
p-TSA para-toluenesulfonic acid
PyBOP (benzotriazol-1-yloxyl)tripyrrolidinophosphonium
RT Reverse transcription
s secondary
S sulfur
t tertiary
THF tetrahydrofuran
TLC thin layer chromatography 1. Chemical Examples—Synthesis and Methods of Preparation Compounds of the invention can be synthesized by methods described herein, and/or according to methods known to one of ordinary skill in the art in view of the description herein.
Instrumentation.

Proton and carbon-13 nuclear magnetic resonance ($^1$H NMR and $^{13}$C NMR) spectra were recorded with a Varian inverse probe 600 INOVA spectrometer. Chemical shifts are recorded in parts per million on the δ scale and are referenced from the residual protium in the NMR solvent, (CHCl$_3$: δ 7.24) for $^1$H NMR, and the carbon resonances of the solvent, (CDCl$_3$: δ 77.2) for $^{13}$C NMR, respectively. Data is reported as follows: chemical shift multiplicity (s=singlet, d=doublet, t=triplet, q=quartet, m=multiplet, br=broad), and coupling constant(s) in Hertz, integration. High resolution mass spectra (HRMS) were recorded on a Bruker APEX 4.7 Tesler FTMS spectrometer using electrospray ion source (ESI). The intermediates and final product were purified with a CombiFlash RF system (Teledyne Isco). Organic solutions were concentrated on Büchi R-205 rotary evaporators. The enantiomeric purities were checked with Berger Supercritical Fluid Chromatography (SFC) and an AS-H column. The enantiomeric preparative purification was performed with Agilent High Pressure Liquid Chromatography and an OD-H column.

Compounds used in the methods of the invention can be prepared by a variety of methods. For instance, the chemical Examples provided herein below provide synthetic schemes for the preparation of the Compound 1 (as the racemate) and the enantiomers (S)-Compound 1 and (R)-Compound 1 (see Schemes S1 and S2 in Examples). A variety of compounds of Formulas (I)-(III) can be prepared by analogous methods with substitution of appropriate starting materials.

General Scheme 1:
Starting from S8, the desired esters can be prepared as shown in General Scheme 1, below.

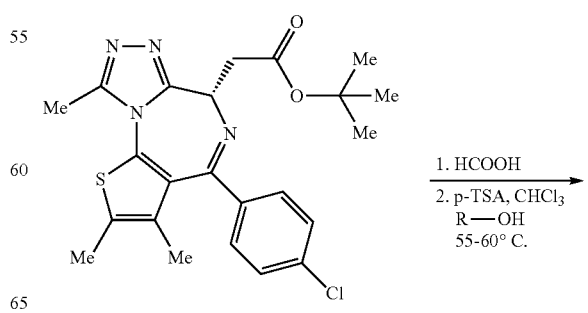

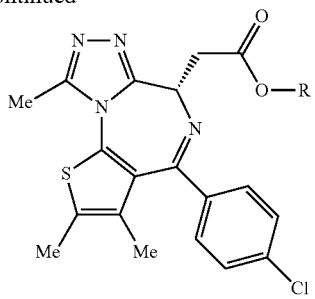

As shown in General Scheme 1, hydrolysis of the t-butyl ester of S8 affords the carboxylic acid, which is treated with p-toluenesulfonic acid (p-TSA) and the desired alcohol in chloroform to provide the desired ester (e.g., a compound of anyone of Formulas (I)-(III)). Acids that can be used for the hydrolysis of the t-butyl ester include, but are not limited to, formic acid, trifluoroacetic acid, hydrochloric acid, acetic acid, and sulfuric acid or a combination thereof.

GENERAL SCHEME 2: Synthesis of Compounds of Formula (I) Starting from Racemic JQ-1

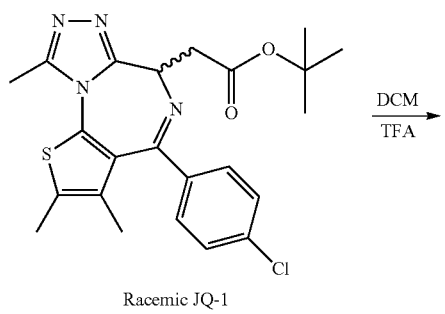

Racemic JQ-1

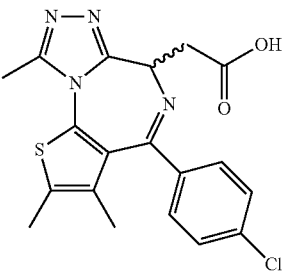

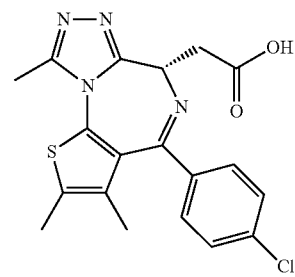

Cinchonidine

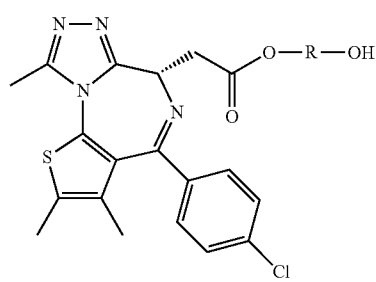

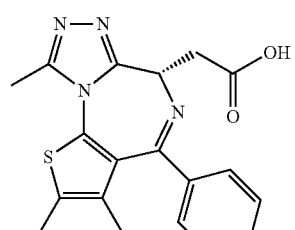

INTERMEDIATE S-4

HO—R—OH
Compound 1: 1,4-cyclohexanediol
Compound 2: Propylene glycol
Compound 3: Ethylene glycol
Compound 4: 1,3-Propylenediol
Compound 5: 1,6-Hexanediol
Compound 6: Glycerol
Compound 7: trans-2,3-Dibromo-2-butene-1,4-diol Scheme S1. Synthesis of Compound 1-Example 1

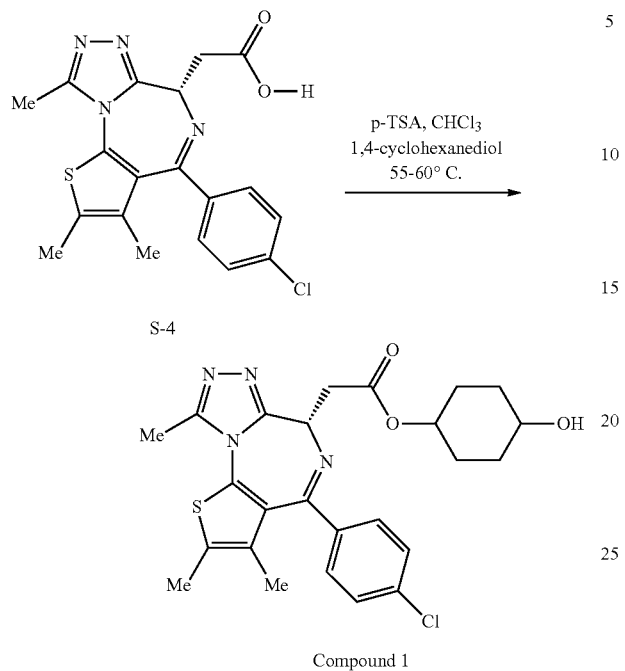

Compound 1

Scheme S2. Synthesis of Compound 2-Example 2

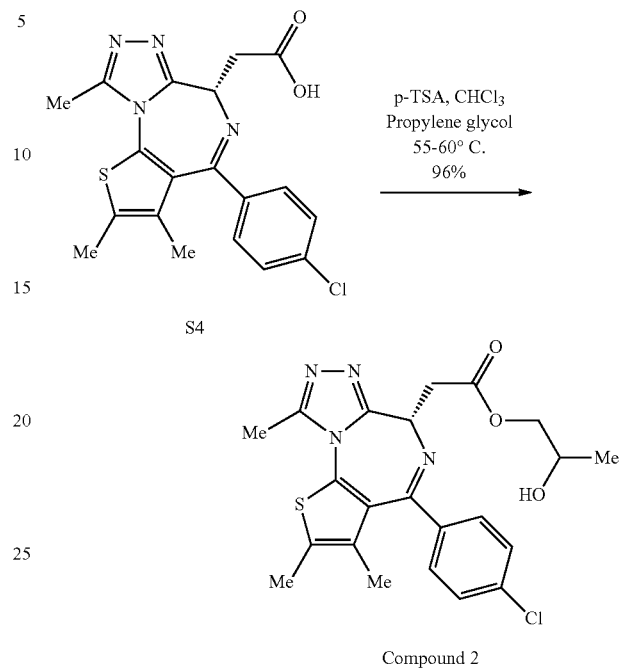

Compound 2

Step 1: Intermediate S-4 was prepared according to "General Scheme 2."

Step 2: P-toluenesulfonic acid (0.3 g, 0.1 equiv.) was added to a solution of 1,4-cyclohexanediol (14 g, 10 equiv.; CAS No. 556-48-9, mixture of cis and trans) and S4 (5 g, 1 equiv.) in chloroform (200 mL) under an atmosphere of nitrogen and at a temperature of 55° C. to 60° C. over 6 hours. The reaction was monitored by HPLC. After 24 hours, HPLC indicated 94% conversion. The reaction mixture was cooled to room temperature and aqueous saturated sodium bicarbonate solution was added to quench the reaction. The organic and aqueous layers were separated, and the organic layer was washed with saturated sodium bicarbonate solution (10 mL/g) and water (10 mL/g), dried with MgSO$_4$, filtered and concentrated under reduced pressure to provide a light brown semi-solid. The residue was purified by flash column chromatography (gradient 0% to 5% methanol-ethyl acetate) to afford Compound 1 as off-white solid. The off-white solid was dissolved in methyl tert-butyl ether (MBTE) and Compound 1 was triturated from the solution by adding heptane (~50 Ml MBTE/heptanes). The solid was filtered and dried under vacuum at 35° C. overnight. The desired product, Compound 1, was isolated as a solid (3.6 g, 59%).

Figure 9:
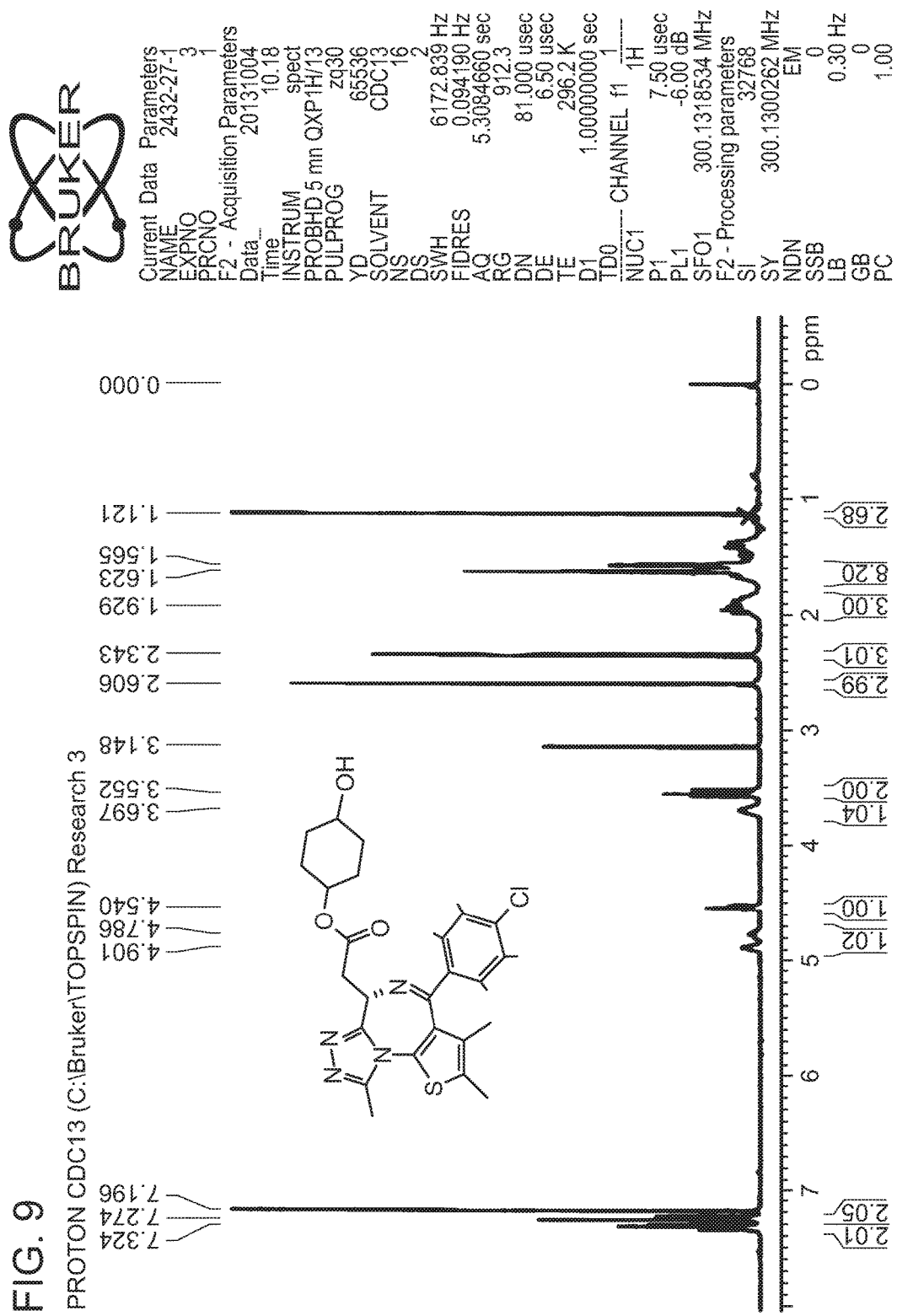
FIG. 9 shows the $^1$H NMR spectra of Compound 1 in $CDCl_3$.

$^1$H NMR (300 MHz, CDCl$_3$, 25° C.) is shown in FIG. 9. HRMS(ESI) calc'd for C$_{25}$H$_{27}$ClN$_4$O$_3$S [M+H]$^+$: 499.02, found 499.2 m/z.

Step 1: Intermediate S-4 was prepared according to "General Scheme 2."

Step 2: P-toluenesulfonic acid (0.3 g, 0.1 equiv.) was added to a solution of propylene glycol (9.5 g, 10 equiv.; CAS No. 57-55-6, racemic) and S4 (5 g, 1 equiv.) in chloroform (200 mL) under an atmosphere of nitrogen and at a temperature of 55 OC to 60° C. over 6 hours. The reaction was monitored by HPLC. After 36 hours, HPLC indicated 93% conversion. The reaction mixture was cooled to room temperature and aqueous saturated sodium bicarbonate solution was added to quench the reaction. The organic and aqueous layers were separated, and the organic layer was washed with saturated sodium bicarbonate solution (10 mL/g) and water (10 mL/g), dried with MgSO$_4$, filtered and concentrated under reduced pressure to provide a light brown semi-solid. The residue was purified by flash column chromatography (gradient 0% to 5% methanol-ethyl acetate) to afford Compound 2 as off-white solid. The off-white solid was dissolved in methyl tert-butyl ether (MBTE) and Compound 2 was triturated from the solution by adding heptane (~50 mL MBTE/heptanes). The solid was filtered and dried under vacuum over at 35° C. overnight. The desired product, Compound 2, was isolated as a white solid (5.5 g, 96%).

Figure 10:
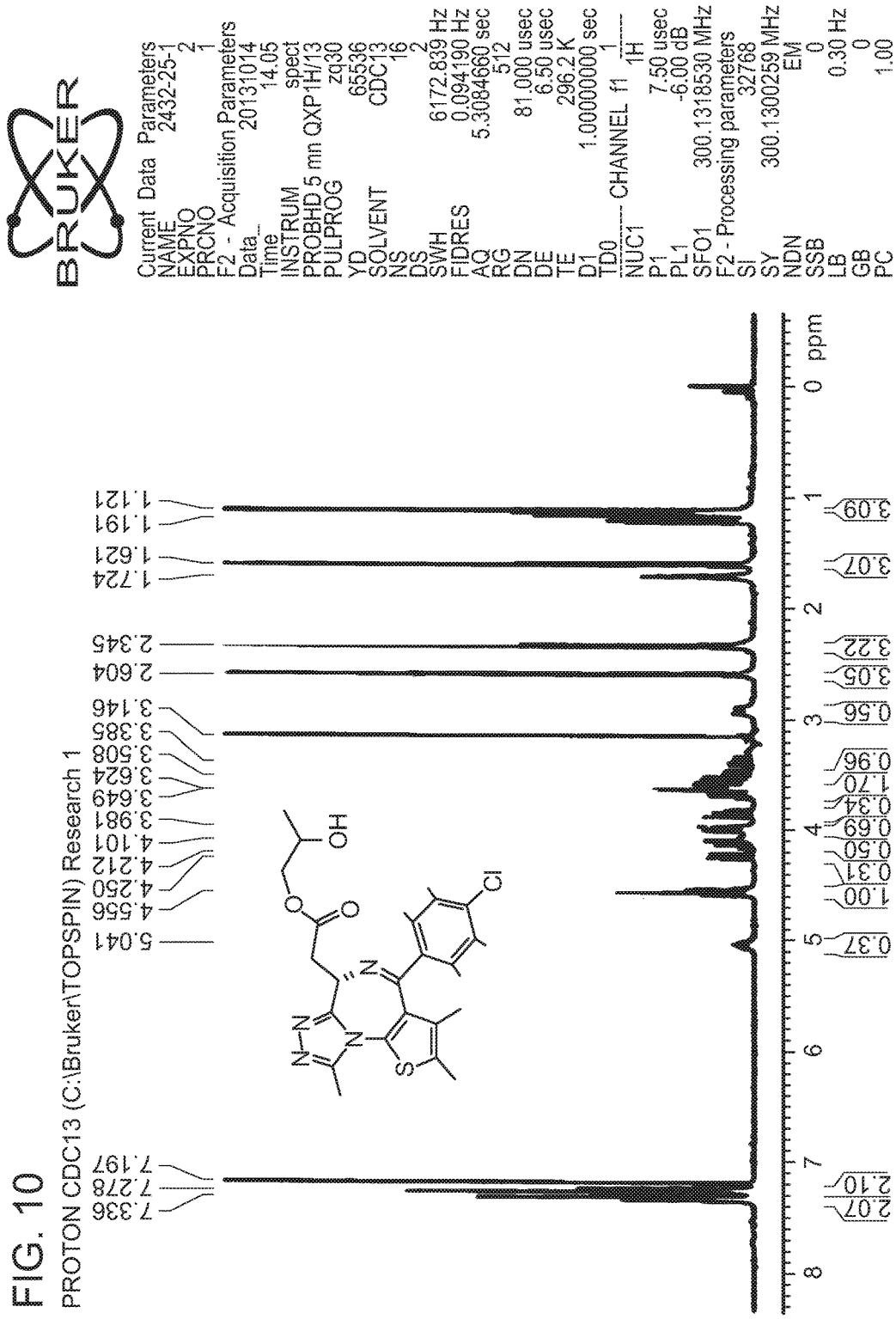
FIG. 10 shows the $^1$H NMR spectra of Compound 2 in $CDCl_3$.
Figure 11:
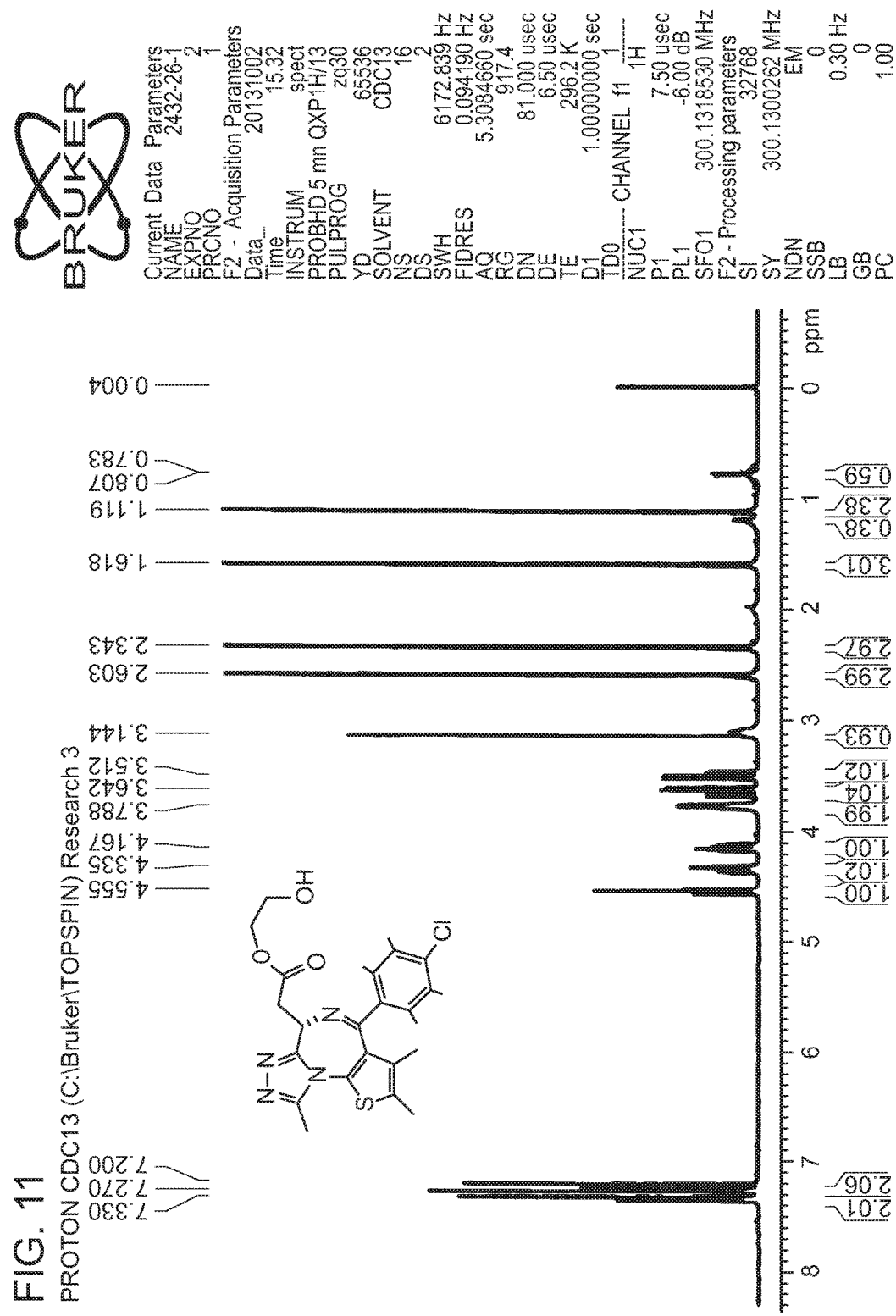
FIG. 11 shows the $^1$H NMR spectra of Compound 3 in $CDCl_3$.
Figure 12:
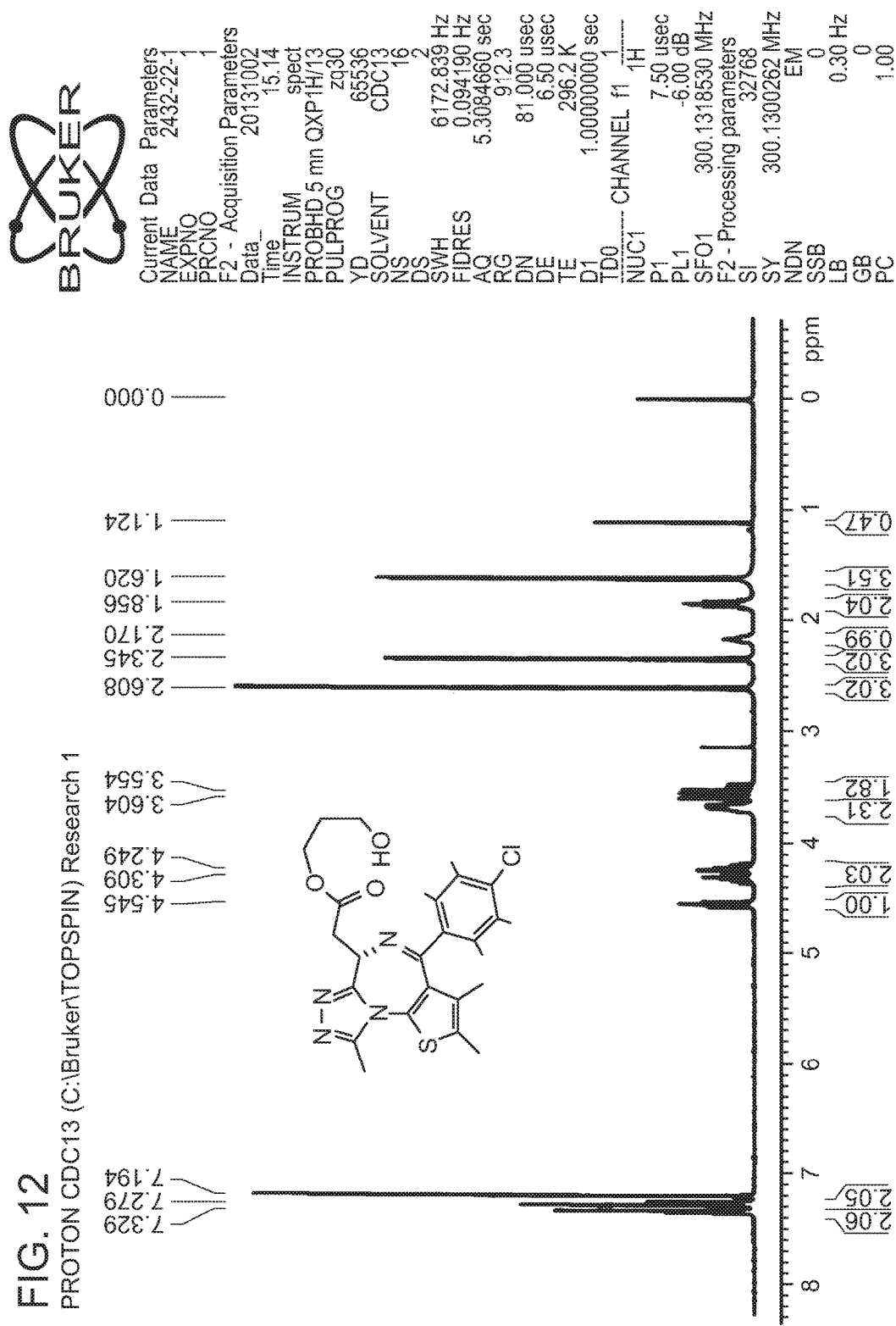
FIG. 12 shows the $^1$H NMR spectra of Compound 4 in $CDCl_3$.
Figure 13:
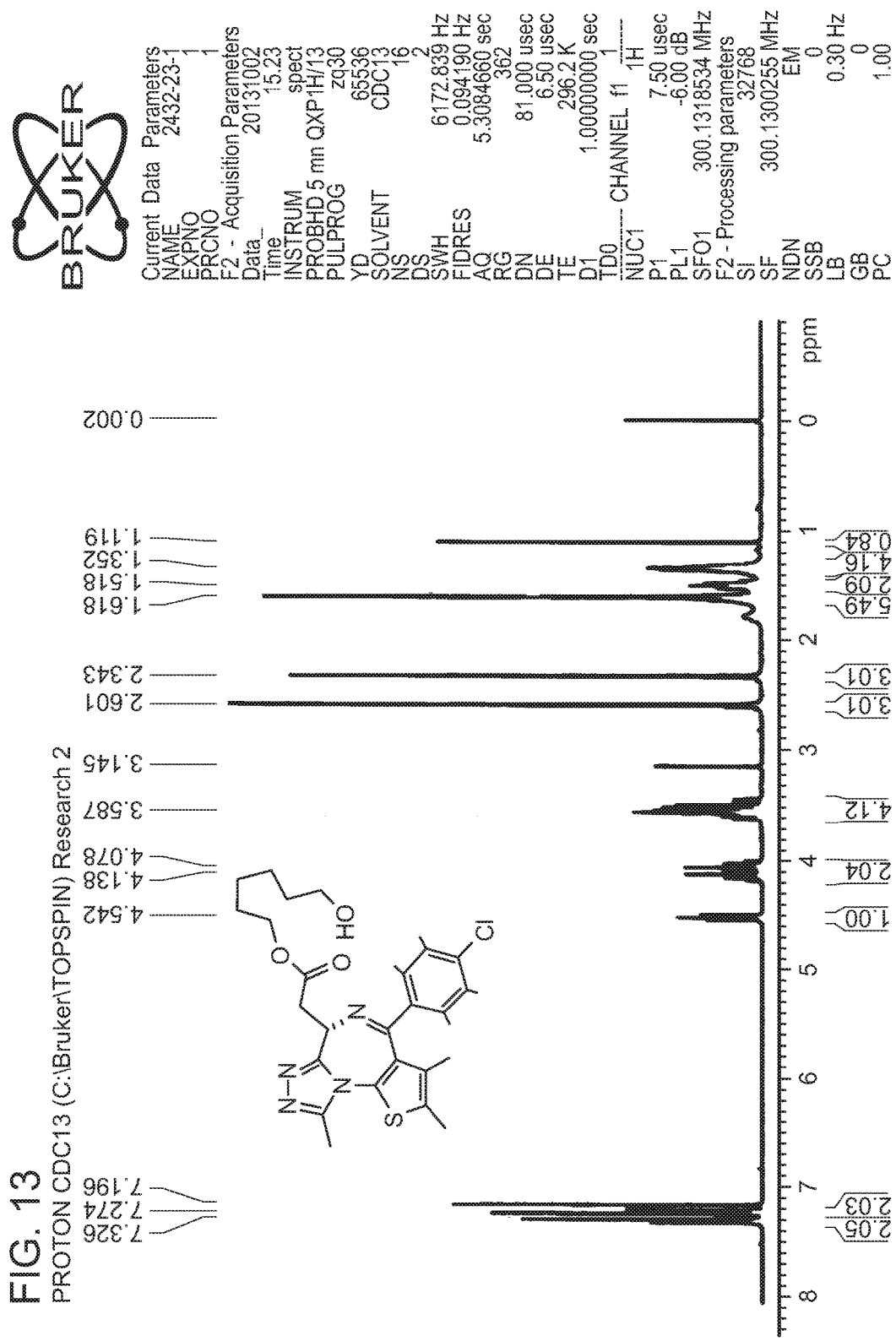
FIG. 13 shows the $^1$H NMR spectra of Compound 5 in $CDCl_3$.
Figure 14:
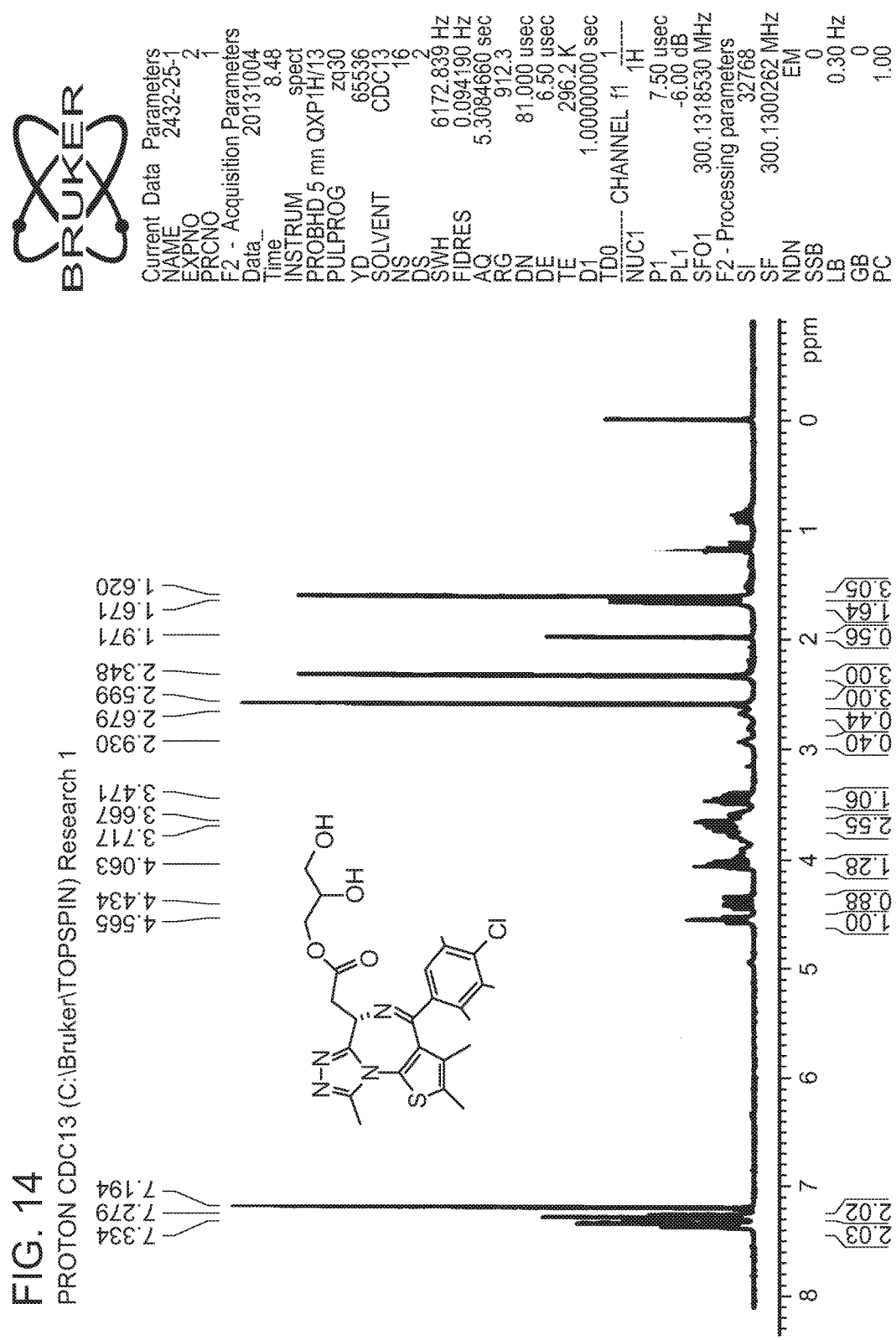
FIG. 14 shows the $^1$H NMR spectra of Compound 6 in $CDCl_3$.
Figure 15:
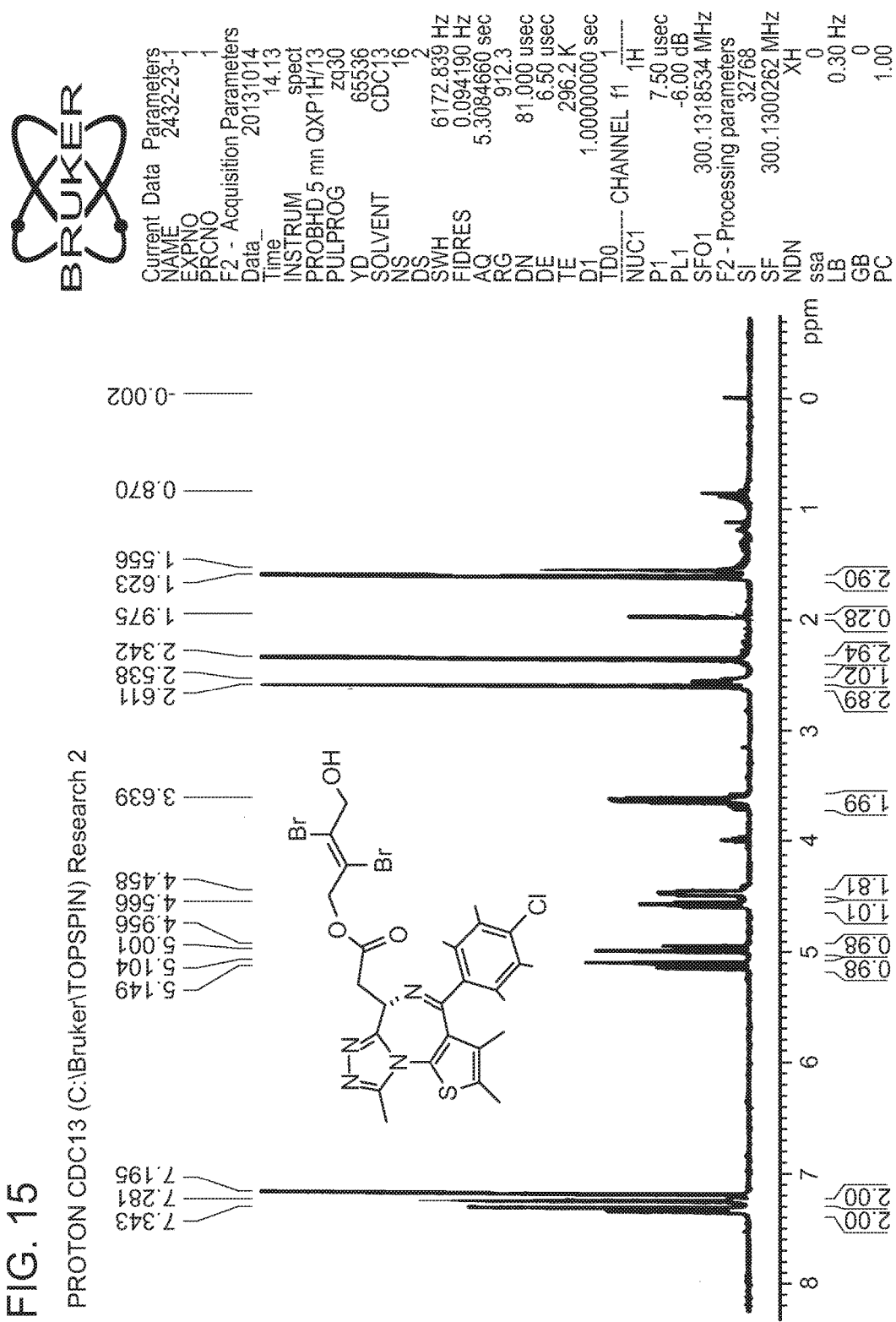
FIG. 15 shows the $^1$H NMR spectra of Compound 7 in $CDCl_3$.

$^1$H NMR (300 MHz, CDCl$_3$, 25° C.) is shown in FIG. 10. HRMS(ESI) calc'd for C$_{22}$H$_{23}$ClN$_4$O$_3$S [M+H]: 458.96, found 459.1 m/z.

Compounds 3-7 were made in accordance with the procedures used for Compounds 1 and 2 above and set out in the General Scheme. The structure of Compounds 3-7 is provided in Table A along with the Mass Spectral data. The NMR for Compounds 3-7 are found in FIGS. 11-15.

TABLE A

| Compound No. | Structure | MS [M + H]+ m/z (Observed) |
|---|---|---|
| Cmpd. 3 | 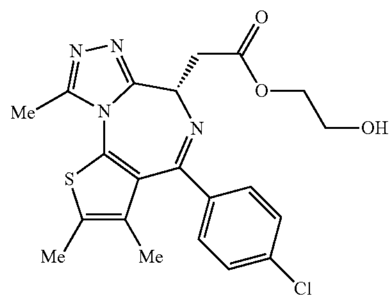 [SMILES: Cc1sc2c(c1C)C(c1ccc(Cl)cc1)=N[C@@H](CC(=O)OCCO)c1nnc(C)n1-2] | 445.3 |
| Cmpd. 4 | 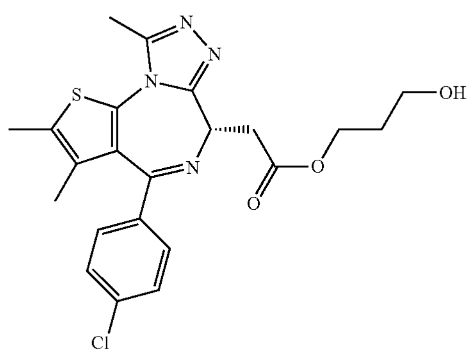 [SMILES: Cc1sc2c(c1C)C(c1ccc(Cl)cc1)=N[C@@H](CC(=O)OCCCO)c1nnc(C)n1-2] | 459.1 |
| Cmpd. 5 | 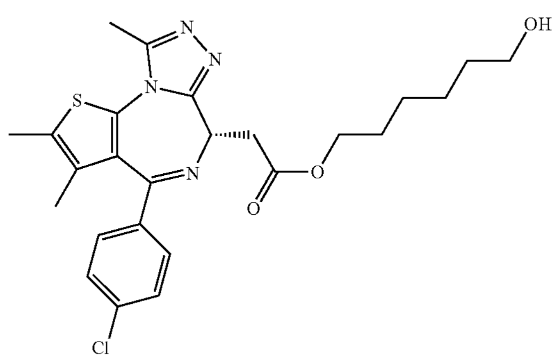 [SMILES: Cc1sc2c(c1C)C(c1ccc(Cl)cc1)=N[C@@H](CC(=O)OCCCCCCO)c1nnc(C)n1-2] | 502.2 |
| Cmpd. 6 | 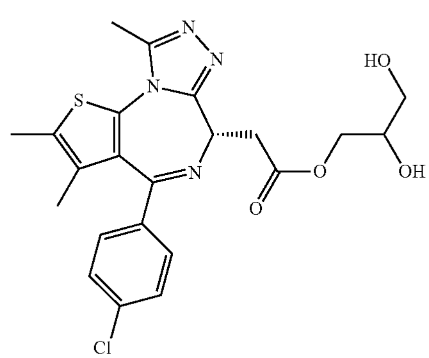 [SMILES: Cc1sc2c(c1C)C(c1ccc(Cl)cc1)=N[C@@H](CC(=O)OCC(O)CO)c1nnc(C)n1-2] | 475.1 |

TABLE A-continued

| Compound No. | Structure | MS [M + H]+ m/z (Observed) |
|---|---|---|
| Cmpd. 7 | (structure shown) | 629 |

Spectral data for each compound were consistent with the assigned structure. (See FIGS. 11-15).

II. Biological Activity

Example 3: Rat Insulinoma Cell Assay

A Cell Titer-Glo assay was utilized to test the sensitivity of four rat insulinoma (RIN) cell lines, RIN-14B, RIN-m5F, RIN-m, and RIN-5, to Compound 1 and Compound 2.

Cells were seeded at 5000 cells per well in a 96-well microculture plate in a total volume of 100 μl/well and incubated for 24 hours. 100 μl of 2× testing compounds (Compound 1 or Compound 2), serially diluted 1:4 were added to each well. The concentrations tested for Compound 1 and Compound 2 were 20 μM, 5 μM, 1.25 μM, 0.313 μM, 0.0781 μM, 0.0195 μM, 0.00488 μM, 0.00122 μM, 0.000305 μM, and 0.0000763 μM. After 168-192 total hours of culture 100 μl of media was removed from each well and 50 μl of Cell Titer-Glo (Promega #G7571) was added to each well. The plate was shaken for 2 minutes and allowed to equilibrate for 10 minutes. Luminescence was measured on a Tecan GENios microplate reader. Percent inhibition of cell proliferation was calculated relative to untreated control wells. All tests were performed in triplicate or quadruplicates at each concentration level. $IC_{50}$ values were calculated using Prism 6.00 curve-fitting with a four parameter-logistic equation.

Results

All cell lines were sensitive to Compound 1 with $IC_{50}$ values under 40 nM and to Compound 2 under 80 nM. These results indicate that BET bromodomain inhibitors are highly effective in decreasing the proliferation of insulinoma cell lines. Results are shown below in Table B.

TABLE B

| | $IC_{50}$ Values (nM) | |
|---|---|---|
| Cell Line | Compound 1 | Compound 2 |
| RIN-14B | 9.3 | 26.5 |
| RIN-m5F | 11.3 | 42.3 |
| RIN-m | 12.6 | 41.5 |
| RIN-5F | 21.6, 19.5 | 64.5, 59.9 |

Example 4: BROMOscan Binding Assay

A BROMOscan binding assay was utilized to test the in vitro binding activity of (S)-Compounds 1, 2, 3, 4, 5 and 7 to the first and second bromodomains (BRD4(1) and BRD4 (2)), separately, of Brd4. (S)-JQ (S8) was used as a positive control.

T7 phage strains displaying bromodomains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (5,000×g) and filtered (0.2 μm) to remove cell debris. Streptavidin-coated magnetic beads were treated with biotinylated small molecule or acetylated peptide ligands for 30 minutes at room temperature to generate affinity resins for bromodomain assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding.

Binding reactions were assembled by combining bromodomains, liganded affinity beads, and test compounds in 1× binding buffer (17% SeaBlock, 0.33×PBS, 0.04% Tween 20, 0.02% BSA, 0.004% Sodium azide, 7.4 mM DTT). Test compounds were prepared as 1000× stocks in 100% DMSO and subsequently serially diluted 1:10 in monoethylene glycol (MEG) to create stocks at 100× the screening concentration (resulting stock solution is 10% DMSO/90% MEG). The compounds were then diluted directly into the assays such that the final concentration of DMSO and MEG were 0.1% and 0.9%, respectively. All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 2 μM nonbiotinylated affinity ligand) and incubated at room temperature with shaking for 30 minutes. The bromodomain concentration in the eluates was measured by qPCR.

Most Kds were determined using a compound top concentration=10,000 nM. If the initial Kd determined was <0.169 nM (the lowest concentration tested), the measurement was repeated with a serial dilution starting at a lower top concentration. A Kd value reported as 40,000 nM indicates that the Kd was determined to be >10,000 nM.

Figure 2:
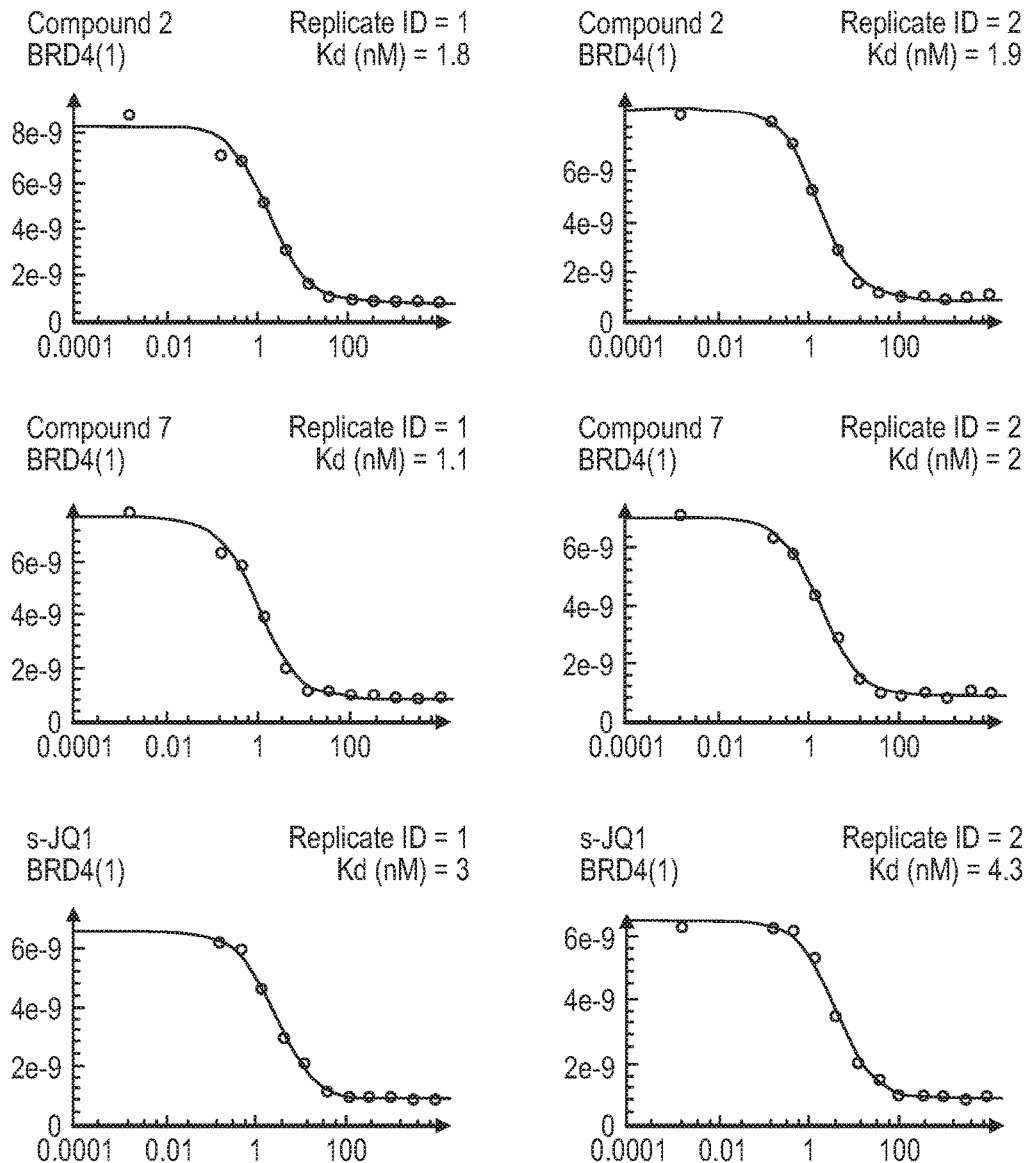
FIG. 2 shows graphs of the BRD4(1) binding activity of Compound 2, Compound 7, and (S)-JQ1, the positive control.
Figure 3:
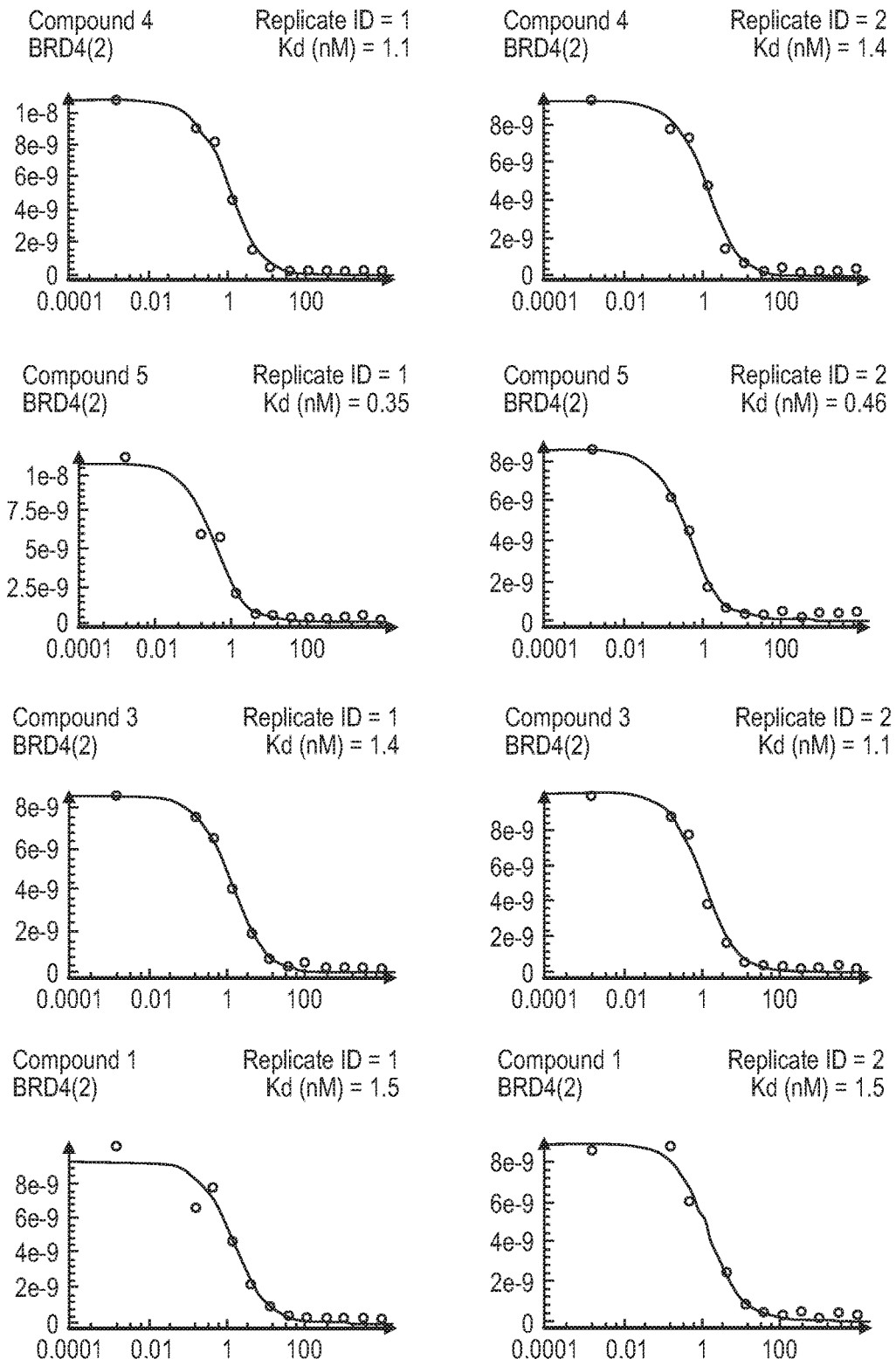
FIG. 3 shows graphs of the BRD4(2) binding activity of Compounds 1, 3, 4 and 5.
Figure 4:
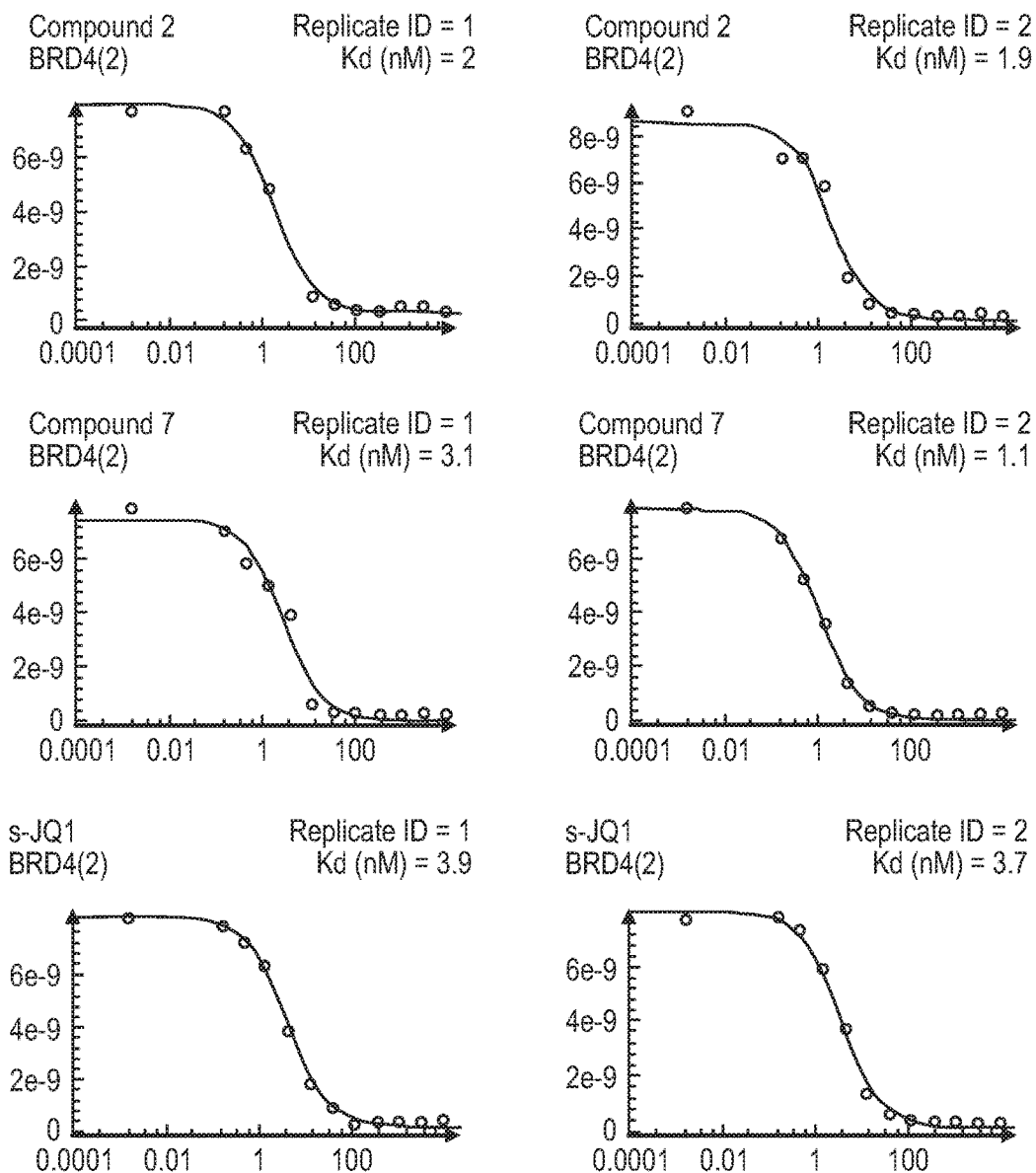
FIG. 4 shows graphs of the BRD4(2) binding activity of Compound 2, Compound 7, and (S)-JQ1, the positive control
Figure 5:
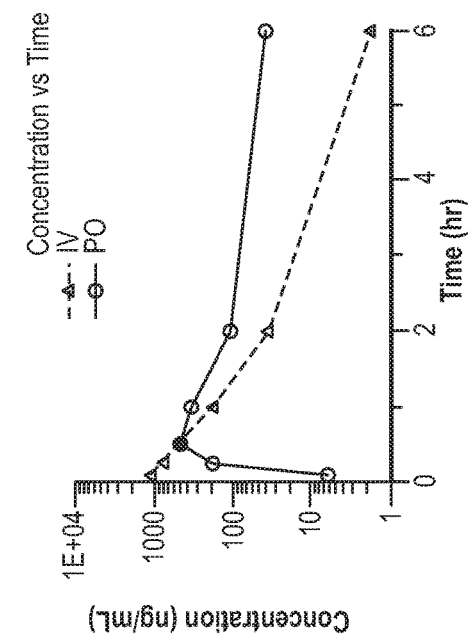
FIG. 5 is a graph showing the plasma concentration of Compound 1 versus time following both IV and oral administration of Compound 1 to Male Sprague-Dawley rats.
Figure 6:
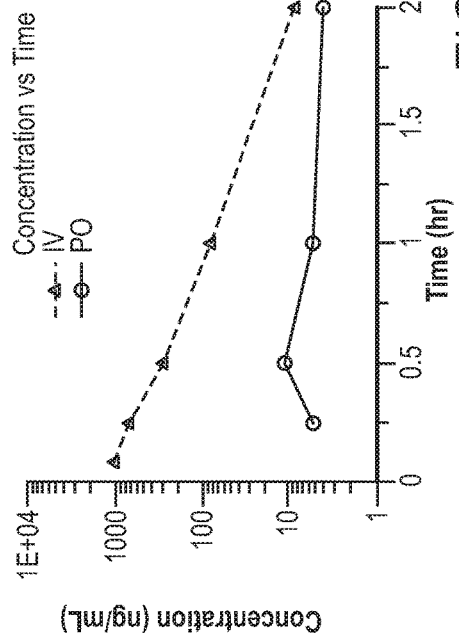
FIG. 6 is a graph showing the plasma concentration of Compound 2 versus time following both IV and oral administration of Compound 2 to Male Sprague-Dawley rats.
Figure 7:
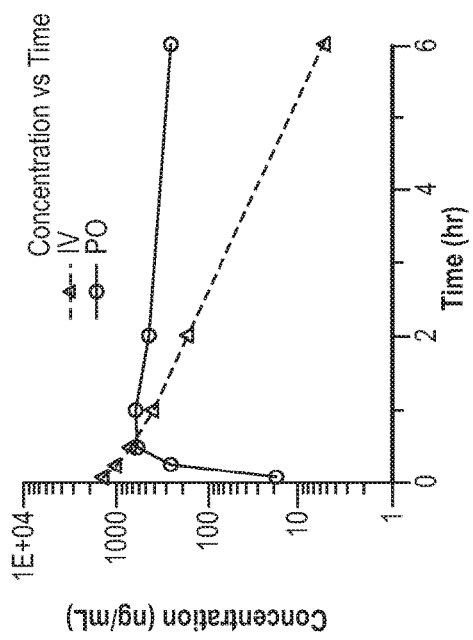
FIG. 7 is a graph showing the plasma concentration of Compound 4 versus time following both IV and oral administration of Compound 4 to Male Sprague-Dawley rats.
Figure 8:
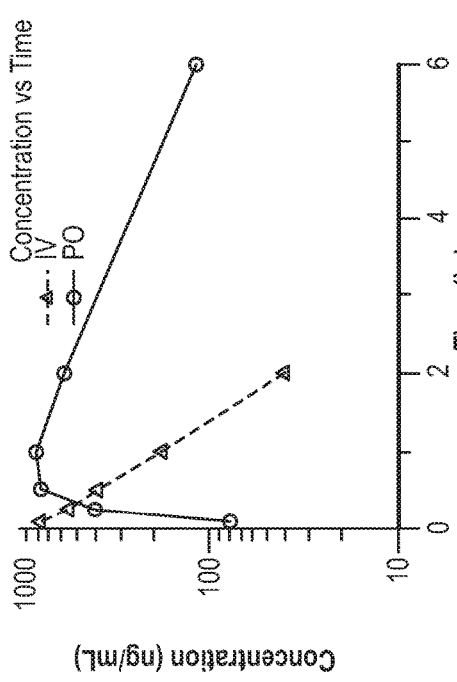
FIG. 8 is a graph showing the plasma concentration of Compound 5 versus time following both IV and oral administration of Compound 5 to Male Sprague-Dawley rats.

Binding constants (Kds) were calculated with a standard dose-response curve using the Hill equation. The Hill Slope was set to −1. Curves were fitted using a non-linear least square fit with the Levenberg-Marquardt algorithm. FIGS. 1-3 show the curve images for all the compounds tested. The amount of bromodomain was measured by qPCR (y-axis) and was plotted against the corresponding compound concentration in nM in log 10 scale.

Results of the binding assay are shown below in Table C.

TABLE C

| Compound | | $K_d$ (nM) | |
|---|---|---|---|
| Name | Structure | BRD4(1) | BRD4(2) |
| (S)-JQ1 | | 3.6 | 3.8 |
| Compound 1 | | 1.3 | 1.5 |
| Compound 2 | | 1.9 | 1.9 |
| Compound 3 | | 1.1 | 1.2 |

TABLE C-continued

| Compound | | $K_d$ (nM) | |
|---|---|---|---|
| Name | Structure | BRD4(1) | BRD4(2) |
| Compound 4 | 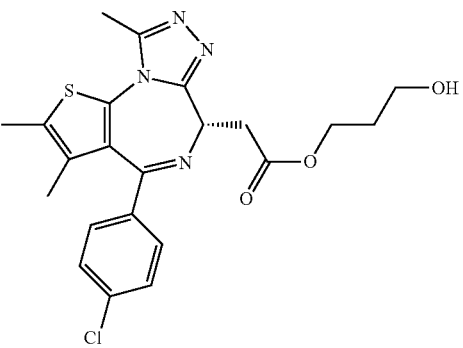 [SMILES: Cc1sc2c(c1C)C(c1ccc(Cl)cc1)=N[C@@H](CC(=O)OCCCO)c1nnc(C)n1-2] | 1.1 | 1.3 |
| Compound 5 | 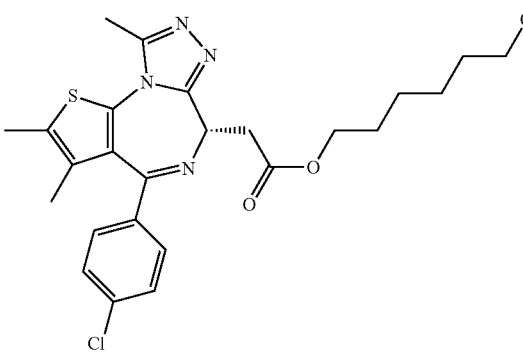 | 0.43 | 0.4 |
| Compound 7 | 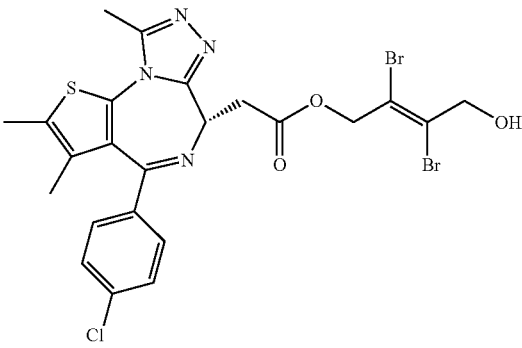 [SMILES: Cc1sc2c(c1C)C(c1ccc(Cl)cc1)=N[C@@H](CC(=O)OC/C(Br)=C(\Br)CO)c1nnc(C)n1-2] | 1.5 | 2.1 |

Results (S)-JQ1 and Compounds 1, 2, 3, 4, 5, and 7 produced low Kd values in the BROMOscan screen binding assay for both BRD4(1) and BRD4(2). These results show that all compounds exhibit excellent in vitro binding activity to both BRD4(1) and BRD4(2) with Kd values comparable or better than that of (S)-JQ1, a known bromodomain inhibitor.

Example 5: Caco-2 Permeability Assay

A Caco-2 Assay was utilized to access intestinal transport and to predict absorption rates and oral bioavailability for Compounds 1-7. (S)-JQ1 (S8) was used as a positive control. Rantidine, warfarin were used as control compounds.

Caco-2 Culture Media containing DMEM, FCS 10%, L-Glutamine 1%, PenStrep 1% (sterile-filtered) was prepared. CacoReady 24 well transwell plate, was used (obtained from ADMEcell (Alameda, Calif.; www.admecell.com) or pre-plated cells made in-house).

A basal plate for changing the media was prepared by filling all wells of a 24 well sterile plate with 900 μl of Caco-2 media and placed in incubator until use. A CacoReady 24 well transwell plate was also placed in a 37° C., 5% $CO_2$ incubator for 4 hours. At the end of the 4 hour incubation, the CacoReady plate and the basal plate were removed and transferred to biosafety hood. The apical section of plate was lifted out and lowered onto empty basal plate. 200 μl of the transport media from the apical compartment of CacoReady plate was aspirated and replaced with 200 μl of fresh media. This was repeated two additional times for a total of 3 washes and the apical section of the CacoReady plate was returned to basal plate and both plates were returned to incubator.

One or two days prior to assay, fresh basal plate was prepared by adding 900 μl of cell media to all wells and placing the basal plate in incubator. The CacoReady plate was transferred from incubator to hood and 200 μl of media from the apical wells were removed and replaced with 200

µl of fresh media. Both the basal plate and the CacoReady plate were returned to the incubator.

On the day of assay, ~5 ml solutions containing of 1000-fold diluted compound solution were prepared in transport buffer (200 µl/insert/well (apical application); 780 µl/insert/well (basal application)). 750 µl of transport buffer to A-B wells and 780 µl of diluted compound solution to B-A wells were added to the basal plate and the plate was placed in the incubator.

The CacoReady plate was placed in a hood and the apical section of plate was lifted out and lowered onto an empty basal plate. 200 µl of the Caco-2 media was removed from the apical wells and replaced with 200 µl of fresh transport media. This was repeated two additional times for a total of 3 washes. 200 µl of the media was removed from the apical wells and replaced with 200 µl of diluted compound (for A-B wells) or 200 pt of fresh transport buffer (for 13-A wells).

The basal plate was then removed from incubator and the apical section of the plate was transferred to the basal plate. Three replicate 10 µl samples from the apical and basal compartments were then collected for $T_0$ and the assay plate was covered and returned to the incubator. $T_0$ samples were diluted with 40 µl transport buffer, quenched with 100 µl quench solution and kept cold.

After 2 hours, three replicate 10 µl samples were collected from all apical compartments and B-A basal compartments and three replicate 50 µl samples were collected from A-B basal compartments. The 10 µl samples were diluted with 40 µl transport buffer and then 100 µl of quench solution was added to all 10 µl and 50 µl samples. 50 µl of all $T_0$ and $T_{2hrs}$ samples were transferred to sample plates and diluted with 100 µl of MilliQ water in preparation for bioanalysis.

Analyte levels (peak area ratios) were measured on apical (A) and basolateral (B) sides at $T_0$ and $T_{2hrs}$. A-to-B and B-to-A fluxes were calculated (mean of n=3 measurements). Apparent permeability (Papp, cm/sec) was calculated as dQ (flux)/(dt×Area×Concentration). The efflux ratio is (B-to-A)/(A-to-B) ratio [i.e., Papp(B–A)/Papp(B–A)]. A ratio>2 is evidence of efflux. Pgp efflux ratio was confirmed by testing+/−pgp inhibitor (i.e., dosing solutions prepared with and without verapamil at a final assay concentration of 25 µM). Permeability is considered lower when it is <1×10$^{-6}$ cm/s and higher when it is >1×10$^{-6}$ cm/s. An efflux ratio of >2 indicates potential for the compound to be a substrate for Pgp or other active transporter.

Results of the Caco-2 assay are shown below in Table D.

TABLE D

| Compound Name | Structure | Assay Conc. (µM) | Mean $P_{app}$, A-B ($10^{-6}$ cm/s) | Mean % recovery | A-B permeability ranking |
|---|---|---|---|---|---|
| (S)-JQ1 | 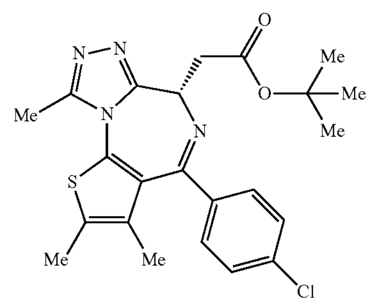 [SMILES: Cc1sc2c(c1C)C(c1ccc(Cl)cc1)=N[C@@H](CC(=O)OC(C)(C)C)c1nnc(C)n1-2] | 10 | 35.4 | 84.6 | Higher |
| Compound 1 | 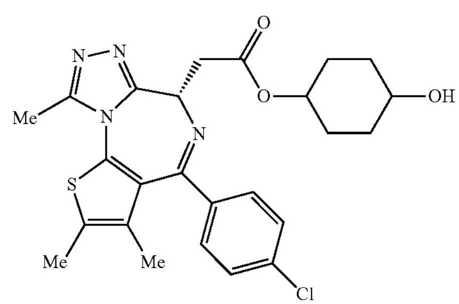 [SMILES: Cc1sc2c(c1C)C(c1ccc(Cl)cc1)=N[C@@H](CC(=O)OC1CCC(O)CC1)c1nnc(C)n1-2] | 10 | 30.7 | 98.5 | Higher |
| Compound 2 | 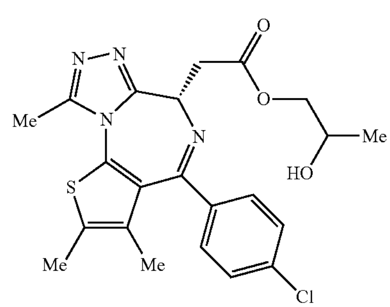 [SMILES: Cc1sc2c(c1C)C(c1ccc(Cl)cc1)=N[C@@H](CC(=O)OCC(C)O)c1nnc(C)n1-2] | 10 | 30.6 | 95.3 | Higher |

TABLE D-continued

| Compound Name | Structure | Assay Conc. (μM) | Mean $P_{app}$, A-B ($10^{-6}$ cm/s) | Mean % recovery | A-B permeability ranking |
|---|---|---|---|---|---|
| Compound 3 | 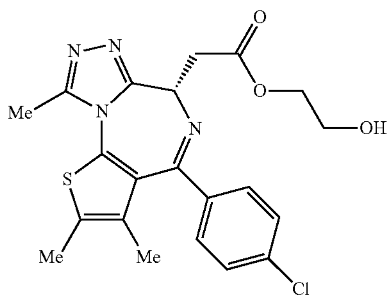 [SMILES: Cc1sc2c(c1C)C(c1ccc(Cl)cc1)=N[C@@H](CC(=O)OCCO)c1nnc(C)n1-2] | 10 | 29.8 | 88.7 | Higher |
| Compound 4 | 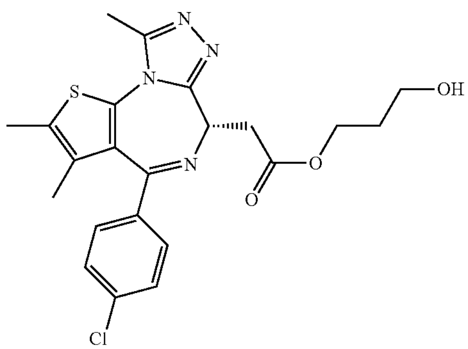 [SMILES: Cc1sc2c(c1C)C(c1ccc(Cl)cc1)=N[C@@H](CC(=O)OCCCO)c1nnc(C)n1-2] | 10 | 35.6 | 99.4 | Higher |
| Compound 5 | 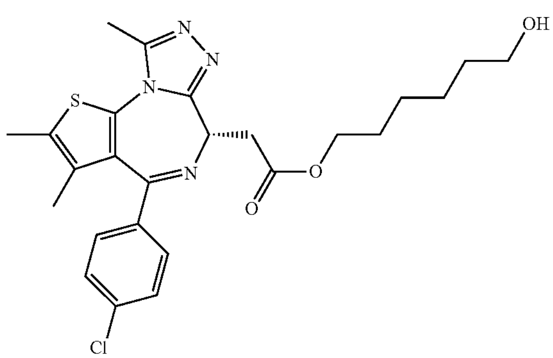 [SMILES: Cc1sc2c(c1C)C(c1ccc(Cl)cc1)=N[C@@H](CC(=O)OCCCCCCO)c1nnc(C)n1-2] | 10 | 39.9 | 88.7 | Higher |
| Compound 6 | 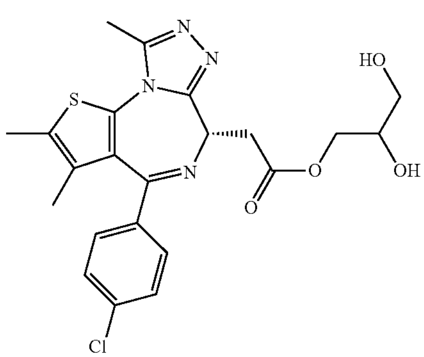 [SMILES: Cc1sc2c(c1C)C(c1ccc(Cl)cc1)=N[C@@H](CC(=O)OCC(O)CO)c1nnc(C)n1-2] | 10 | 4.74 | 90.8 | Higher |

TABLE D-continued

| Compound Name | Structure | Assay Conc. (μM) | Mean $P_{app}$, A-B ($10^{-6}$ cm/s) | Mean % recovery | A-B permeability ranking |
|---|---|---|---|---|---|
| Compound 7 | 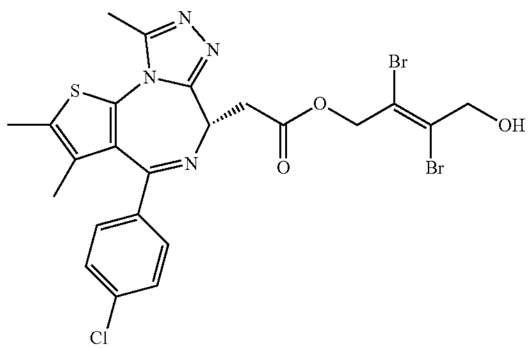 [SMILES: Cc1sc2c(c1C)C(c1ccc(Cl)cc1)=N[C@@H](CC(=O)OC/C(Br)=C(\Br)CO)c1nnc(C)n1-2] | 10 | 31.3 | 76.9 | Higher |
| Ranitidine | | 10 | 0.170 | 97.8 | Lower as expected |
| Warfarin | | 10 | 38.8 | 99.9 | Higher as expected |

Results.

The results in Table D show that Compounds 1-7 have excellent cellular permeability in vitro, and strongly predict oral bioavailability.

Example 6: Oral Availability of Compounds 1-2 and 4-5 in Male Sprague-Dawley Rats To establish whether Compounds 1-2 and 4-5 possess good oral bioavailability, the pharmacokinetic properties of Compounds 1-2 and 4-5 were accessed via intravenous (IV) and oral (PO) administration of the compounds in Male Sprague-Dawley Rats.

Male Sprague-Dawley (~250-325 g) with indwelling jugular vein cannulae (JVC) were purchased and allowed to acclimate to the test facility for a minimum of 2 days. All animals were fasted overnight prior to dosing. Oral formulations were prepared by weighing the appropriate amount of the compound into formulation vial and adding the appropriate volume of DMSO (10%), Solutol HS-15 (10%), and saline (80%) (See Table 0 for compound amounts and concentrations of all formulations). Once the test compound was in the vial, DMSO was added and the vial was vortexed for 1-2 minutes and sonicated for 3 minutes. The appropriate volume of Solutol HS-15 was then added to formulation vial and the vial was vortexed for 1-2 minutes and sonicated for 2 minutes. Saline was added and the pH adjusted to about 6.8-7.4, and the vial was vortexed for 2 minutes.

IV formulations were prepared by placing a 0.8 mL aliquot of the oral formulation into another vial and adding 1.2 mL of IV vehicle (10% EtOH, 10% Cremophor, 80% sterile water. The vial was then vortexed for 2 minutes. The formulation should possess a pH 6.8-7.4 and should be adjusted as-needed.

TABLE E

| Compound name | Structure | Dose Route | Dose Level (mg/kg) | Dose Volume (mL/kg) | Conc (mg/mL) |
|---|---|---|---|---|---|
| Compound 1 | 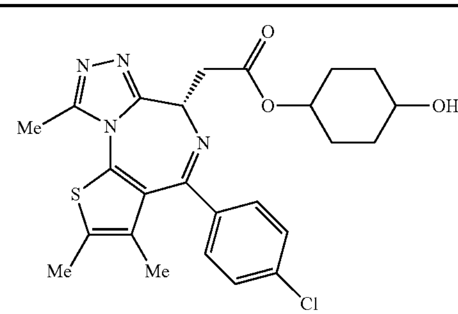 | IV<br>PO | 1<br>5 | 5<br>10 | 0.2<br>0.5 |

TABLE E-continued

| Compound name | Structure | Dose Route | Dose Level (mg/kg) | Dose Volume (mL/kg) | Conc (mg/mL) |
|---|---|---|---|---|---|
| Compound 2 | 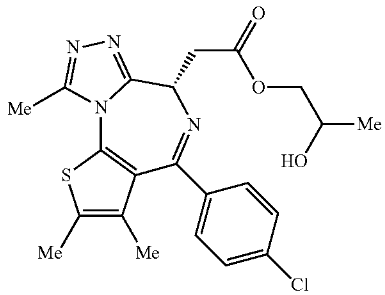 [SMILES: Cc1sc2c(c1C)C(c1ccc(Cl)cc1)=N[C@@H](CC(=O)OCC(C)O)c1nnc(C)n1-2] | IV | 1 | 5 | 0.2 |
| | | PO | 5 | 10 | 0.5 |
| Compound 4 | 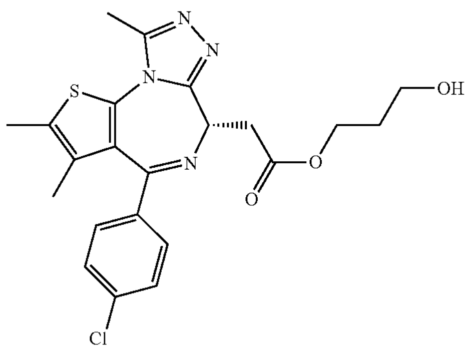 [SMILES: Cc1sc2c(c1C)C(c1ccc(Cl)cc1)=N[C@@H](CC(=O)OCCCO)c1nnc(C)n1-2] | IV | 1 | 5 | 0.2 |
| | | PO | 5 | 10 | 0.5 |
| Compound 5 | 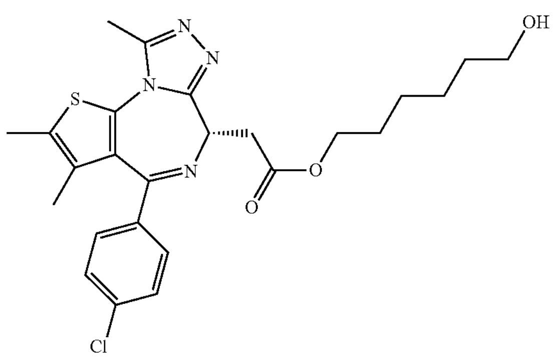 [SMILES: Cc1sc2c(c1C)C(c1ccc(Cl)cc1)=N[C@@H](CC(=O)OCCCCCCO)c1nnc(C)n1-2] | IV | 1 | 5 | 0.2 |
| | | PO | 5 | 10 | 0.5 |

Oral dosing was performed using a ball-tipped gavage needle. All animals were observed at dosing and each scheduled collection. No abnormalities were observed during the course of the study. Serial samples were collected by via tail snip, or facial vein. Blood samples were collected into NaF $Na_2EDTA$ tubes and stored on wet ice until processed to plasma by centrifugation (3500 rpm for 10 minutes at 5° C.) within 30 minutes of collection. Plasma samples were transferred into matrix tubes and stored at −80° C. until transferred to analytical chemistry for analysis. The cellular fraction was discarded. Dose formulation and plasma samples were analyzed for parent drug and metabolite by Agilux Laboratories via LC/MS/MS using an RGA I assay.
Results of are shown below.

| Rat | $T^{1/2}$ (hr) | $T_{max}$ (hr) | $C_{max}$ (ng/mL) | $AUC_{last}$ (hr * ng/mL) | $AUC_{inf}$ (hr * ng/mL) | |
|---|---|---|---|---|---|---|
| Compound 1 IV Dose (1 mg/kg) | | | | | | |
| | | | | | | Extrapolated (%) |
| 5 | 0.798 | 0.083 | 1490 | 1496 | 1502 | 0.41 |
| Compound 1 PO Dose (5 mg/kg) | | | | | | |
| | | | | | | F* (%) |
| 6 | NA | 1.00 | 619 | 2362 | NA | 31.6 |

-continued

| Rat | $T^{1/2}$ (hr) | $T_{max}$ (hr) | $C_{max}$ (ng/mL) | $AUC_{last}$ (hr * ng/mL) | $AUC_{inf}$ (hr * ng/mL) | |
|---|---|---|---|---|---|---|
| Compound 2 IV Dose (1 mg/kg) | | | | | | |
| | | | | | | Extrapolated (%) |
| 7 | 0.457 | 0.083 | 790 | 969 | 593 | 4.62 |
| Compound 2 PO Dose (5 mg/kg) | | | | | | |
| | | | | | | F (%) |
| 8 | 1.78 | 1.00 | 820 | 2721 | 3030 | 102.2 |
| Compound 4 IV Dose (1 mg/kg) | | | | | | |
| | | | | | | Extrapolated (%) |
| 1 | 0.807 | 0.083 | 1130 | 782 | 784 | 0.28 |
| Compound 4 PO Dose (5 mg/kg) | | | | | | |
| | | | | | | F (%) |
| 2 | 1.83 | 0.500 | 480 | 813 | 918 | 23.4 |
| Compound 5 IV Dose (1 mg/kg) | | | | | | |
| | | | | | | Extrapolated (%) |
| 3 | 0.301 | 0.083 | 1070 | 512 | 516 | 0.75 |
| Compound 5 PO Dose (5 mg/kg) | | | | | | |
| | | | | | | F (%) |
| 4 | NA | 0.500 | 12.2 | 12.1 | NA | NA |

NA: Insufficient data available to calculate PK parameter.
$t^{1/2}$ = terminal half-life
$AUC_{0-\infty}$ = area under a conconcetration of analyte vs. time calculated using zero to infinity
$AUC_{0-last}$ = compound from time zero to the time of the last positive Y value
$C_{max}$ = the peak of maximum concentrations
$T_{max}$ = the time of peak concentration
*AUC0-last was used to calculate % F.

Results

The results demonstrate that exposures fr compounds 1, 2, 4 and 5 are detected following IV administration and that compounds 1, 2 and 4 have oral bioavailability with a F>23%.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by Structural Formula III:

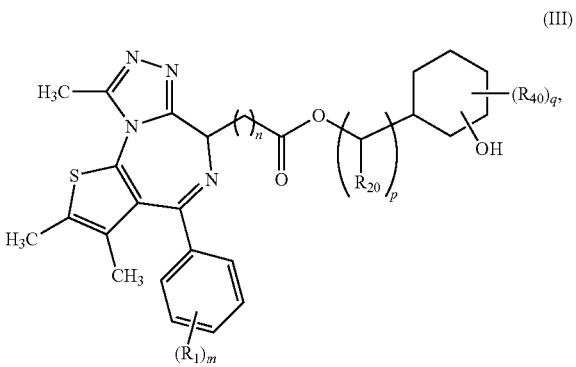

(III)

or a pharmaceutically acceptable salt thereof, wherein:
$R_1$ for each occurence independently is a halogen;
$R_{20}$, for each occurence independently, is —H or a $(C_1-C_3)$ alkyl;
$R_{40}$, for each occurence independently, is —OH, or a $(C_1-C_3)$alkyl;
q is 0, 1, 2, 3 or 4;
n is 1; and
each m and p is independently 0, 1, 2, 3, or 4.

2. The compound of claim 1, wherein p is 0.
3. The compound of claim 1, wherein m is 1.
4. A compound represented by the following formula:

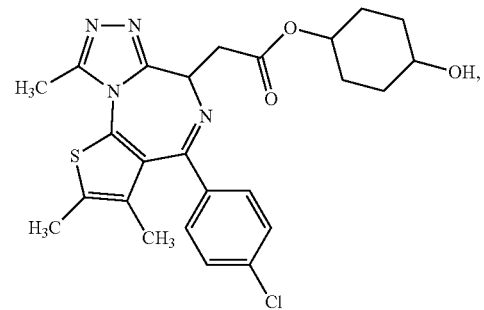

or a pharmaceutically acceptable salt thereof.

5. A compound represented by the following formula:

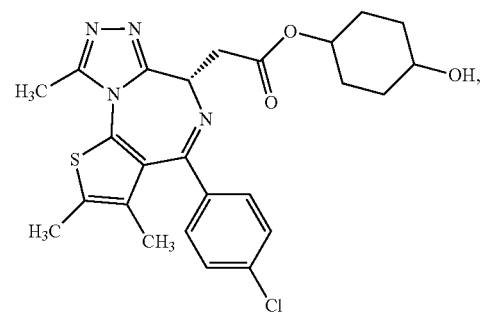 [SMILES: Cc1sc2c(c1C)C(c1ccc(Cl)cc1)=N[C@@H](CC(=O)OC1CCC(O)CC1)c1nnc(C)n1-2]

or a pharmaceutically acceptable salt thereof.

6. A pharmaceutical composition comprising a pharmaceutically acceptable carrier or diluent and a therapeutically effective amount of a compound of claim 1.

7. A method of treating a disorder in a subject in need thereof, comprising administering to the subject an effective amount of a compound according to claim 1, wherein the disorder is selected from: acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Burkitt's lymphoma, MLL driven leukemia chronic lymphocytic leukemia, Eosinophilic Leukemia, Hairy Cell Leukemia, Hodgkin Lymphoma, Multiple Myeloma, Non-Hodgkin Lymphoma.

8. A method of treating a disorder in a subject in need thereof, comprising administering to the subject an effective amount of a compound according to claim 1, wherein the disorder is NUT midline carcinoma.

9. A method of treating a disorder in a subject in need thereof, comprising administering to the subject an effective amount of a compound according to claim 1, wherein the disorder is a condition associated with hyperinsulinaemia selected from: insulinoma, congential hyperinsulism, polycystic ovary syndrome (PCOS), Beckwith-Wiedemann syndrome, or in patients following gastric bypass surgery.

10. A method of reducing male fertility in a subject comprising administering to said subject an effective amount of a compound of claim 1.

* * * * *